(12) United States Patent
Conner et al.

(10) Patent No.: US 8,771,352 B2
(45) Date of Patent: Jul. 8, 2014

(54) METHOD AND APPARATUS FOR TIBIAL FIXATION OF AN ACL GRAFT

(75) Inventors: Nathanael K. Conner, Huntertown, IN (US); Brian K. Berelsman, Warsaw, IN (US); Gregory J. Denham, Warsaw, IN (US); Kevin T. Stone, Winona Lake, IN (US); Nicholas R. Slater, Chandler, AZ (US); Jeffery D. Arnett, Gilbert, AZ (US); Joshua A. Butters, Chandler, AZ (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 288 days.

(21) Appl. No.: 13/109,667

(22) Filed: May 17, 2011

(65) Prior Publication Data

US 2012/0296427 A1 Nov. 22, 2012

(51) Int. Cl.
*A61F 2/08* (2006.01)
*A61F 2/46* (2006.01)

(52) U.S. Cl.
USPC .................... 623/13.13; 623/13.14; 606/86 R

(58) Field of Classification Search
CPC ........................................................ A61F 2/08
USPC ............... 606/103–104, 139, 144–150, 86 R; 623/13.11–13.2
See application file for complete search history.

(56) References Cited

U.S. PATENT DOCUMENTS

| | | | |
|---|---|---|---|
| 65,499 A | 6/1867 | Miller | |
| 126,366 A | 4/1872 | Wills | |
| 233,475 A | 10/1880 | Cook et al. | |
| 261,501 A | 7/1882 | Vandermark | |
| 268,407 A | 12/1882 | Hughes | |
| 330,087 A | 11/1885 | Binns | |
| 401,677 A | 4/1889 | Autenrieth | |
| 417,805 A | 12/1889 | Beaman | |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

Invitation to Pay Additional Fees mailed Jul. 19, 2012, for PCT/US2012/037703 claiming benefit of U.S. Appl. No. 13/109,667, filed May 7, 2011.

(Continued)

*Primary Examiner* — Andrew Iwamaye
(74) *Attorney, Agent, or Firm* — Harness, Dickey

(57) ABSTRACT

A tensioner system for use in tensioning graft strands in a knee reconstruction procedure can include a handle assembly, a tensioner assembly coupled relative to the handle assembly, and a drive shaft slidably received through and supported by the handle assembly. The tensioner assembly can include an arm support member rotatably coupled to the handle assembly and first and second arm members each rotatably coupled to lateral sides of the arm support member. Each arm member can include at least one graft attachment area adapted to be coupled to a graft strand. The arm support member can be configured to rotate about an axis perpendicular to a longitudinal axis of the tensioner system and perpendicular to an axis of rotation of each of the arm members. The drive shaft can include proximal and distal ends that extend beyond respective proximal and distal ends of the handle assembly.

39 Claims, 26 Drawing Sheets

(56) References Cited

U.S. PATENT DOCUMENTS

| | | | |
|---|---|---|---|
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| RE26,501 | E | 12/1968 | Kendrick et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,547,389 | A | 12/1970 | Mitchell |
| 3,579,831 | A | 5/1971 | Stevens et al. |
| 3,590,616 | A | 7/1971 | Schussler et al. |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,907,442 | A | 9/1975 | Reid |
| 3,910,281 | A | 10/1975 | Kletschka et al. |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |
| 3,933,153 | A | 1/1976 | Csatary et al. |
| 3,937,217 | A | 2/1976 | Kosonen et al. |
| 3,943,932 | A | 3/1976 | Woo |
| 3,946,446 | A | 3/1976 | Schofield |
| 3,946,728 | A | 3/1976 | Bettex |
| 3,946,740 | A | 3/1976 | Bassett |
| 3,953,896 | A | 5/1976 | Treace |
| 3,954,103 | A | 5/1976 | Garcia-Roel et al. |
| 3,961,632 | A | 6/1976 | Moossun |
| 3,973,560 | A | 8/1976 | Emmett et al. |
| 3,976,079 | A | 8/1976 | Samuels et al. |
| 3,977,050 | A | 8/1976 | Perez et al. |
| 3,979,799 | A | 9/1976 | Merser et al. |
| 3,985,138 | A | 10/1976 | Jarvik |
| 3,990,619 | A | 11/1976 | Russell |
| 4,005,707 | A | 2/1977 | Moulding, Jr. |
| 4,006,747 | A | 2/1977 | Kronenthal et al. |
| 4,007,743 | A | 2/1977 | Blake |
| 4,013,071 | A | 3/1977 | Rosenberg et al. |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes et al. |
| 4,144,876 | A | 3/1979 | DeLeo |
| 4,146,022 | A | 3/1979 | Johnson et al. |
| 4,149,277 | A | 4/1979 | Bokros |
| 4,157,714 | A | 6/1979 | Foltz et al. |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |

(56) References Cited

U.S. PATENT DOCUMENTS

| | | |
|---|---|---|
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |

(56) References Cited

U.S. PATENT DOCUMENTS

| | | |
|---|---|---|
| 5,007,921 A | 4/1991 | Brown |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |

(56) References Cited

U.S. PATENT DOCUMENTS

| | | |
|---|---|---|
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |

(56) References Cited

U.S. PATENT DOCUMENTS

| | | |
|---|---|---|
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |

(56) References Cited

U.S. PATENT DOCUMENTS

| | | |
|---|---|---|
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |

(56) References Cited

U.S. PATENT DOCUMENTS

| | | | |
|---|---|---|---|
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 * | 10/2002 | Castaneda et al. ............... 606/1 |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Dreyfuss et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |

(56) References Cited

U.S. PATENT DOCUMENTS

| | | | |
|---|---|---|---|
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 * | 10/2007 | Brown et al. ............ 623/13.15 |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |

(56) References Cited

U.S. PATENT DOCUMENTS

| | | |
|---|---|---|
| 8,506,597 B2 | 8/2013 | Kaiser et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1* | 9/2004 | McBrayer ............. 606/142 |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |

(56) References Cited

U.S. PATENT DOCUMENTS

| | | |
|---|---|---|
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1* | 3/2006 | Re et al. ............ 606/72 |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027430 A1 | 1/2008 | Montgomery et al. |
| 2008/0027446 A1 | 1/2008 | Stone et al. |

(56) References Cited

U.S. PATENT DOCUMENTS

| | | |
|---|---|---|
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0026141 A1 | 2/2011 | Barrows |
| 2011/0046733 A1 | 2/2011 | Eggli |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0116409 A1 | 5/2012 | Stone |
| 2012/0123447 A1* | 5/2012 | Corrao et al. ................. 606/144 |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0245585 A1 | 9/2012 | Kaiser et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |

FOREIGN PATENT DOCUMENTS

| | | |
|---|---|---|
| AU | 5850469 | 1/1971 |
| AU | 5963869 | 2/1971 |

(56) References Cited

FOREIGN PATENT DOCUMENTS

| | | |
|---|---|---|
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 3225620 | 2/1983 |
| DE | 3136083 | 3/1983 |
| DE | 4127550 | 2/1993 |
| DE | 4302397 | 7/1993 |
| DE | 19841252 | 3/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0260970 | 3/1988 |
| EP | 0270704 | 6/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0490417 | 6/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |

OTHER PUBLICATIONS

"AperFix® System Surgical Technique Guide. Single Tunnel Double Bundle.™" Cayenne Medical brochure. (Aug. 2008) 8 sheets.

"Arthroscopic Meniscal Repair using the Meniscal Cinch™", Surgical Technique brochure. (2008) Arthrex® 6 sheets.

"Bio-Intrafix Tibial Soft Tissue Fasteners, Building on the Legacy of IntraFix," brochure. DePuy Mitek,(Feb. 2007) 6 sheets.

"Biomechanical Evaluation of the Biomet Sports Medicine Jurggerknot™ Soft Anchor in Porcine Bone," Study completed Jan. 2010. Biomet Sports Medicine Research and Development, Warsaw, Indiana. 2 pages.

"Do your next distal tendon repair with . . . The Lubbers Technique", Teno Fix® brochure, 2003 (2 pages) Ortheon® Medical.

"EZ Loc Femoral Fixation Device," copyright 2005 Arthrotek, Inc. (8 sheets).

(56) References Cited

OTHER PUBLICATIONS

"Juggerknot™ Soft Anchor Midfoot Repair," brochure. Biomet Sports Medicine (Jul. 2011) 12 sheets.
"Juggerknot™ Soft Anchor. It's Small. It's strong. And it's all suture . . . " Ordering Information brochure. Biomet Sports Medicine (Jun. 2011) 2 sheets.
"Juggerknot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (October), 2002: pp. 939-943.
Opus Medical; The AutoCuff System; www.opusmedical.com; 2003.
Patrick Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, a Useful Technique," Texas Heart® Institute. Journal List> Tex Heart Inst J > v.33(4); (2006).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Mar. 6, 2013 for PCT/US2012/062738 which claims benefit of U.S. Appl. No. 13/288,459, filed Nov. 3, 2011.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
International Search Report and Written Opinion mailed Mar. 6, 2014 for PCT/US2013/075989 which claims benefit of U.S. Appl. No. 13/720,648 filed Dec. 19, 2012.
US 6,238,418, 05/2001, Schwartz et al. (withdrawn)

* cited by examiner

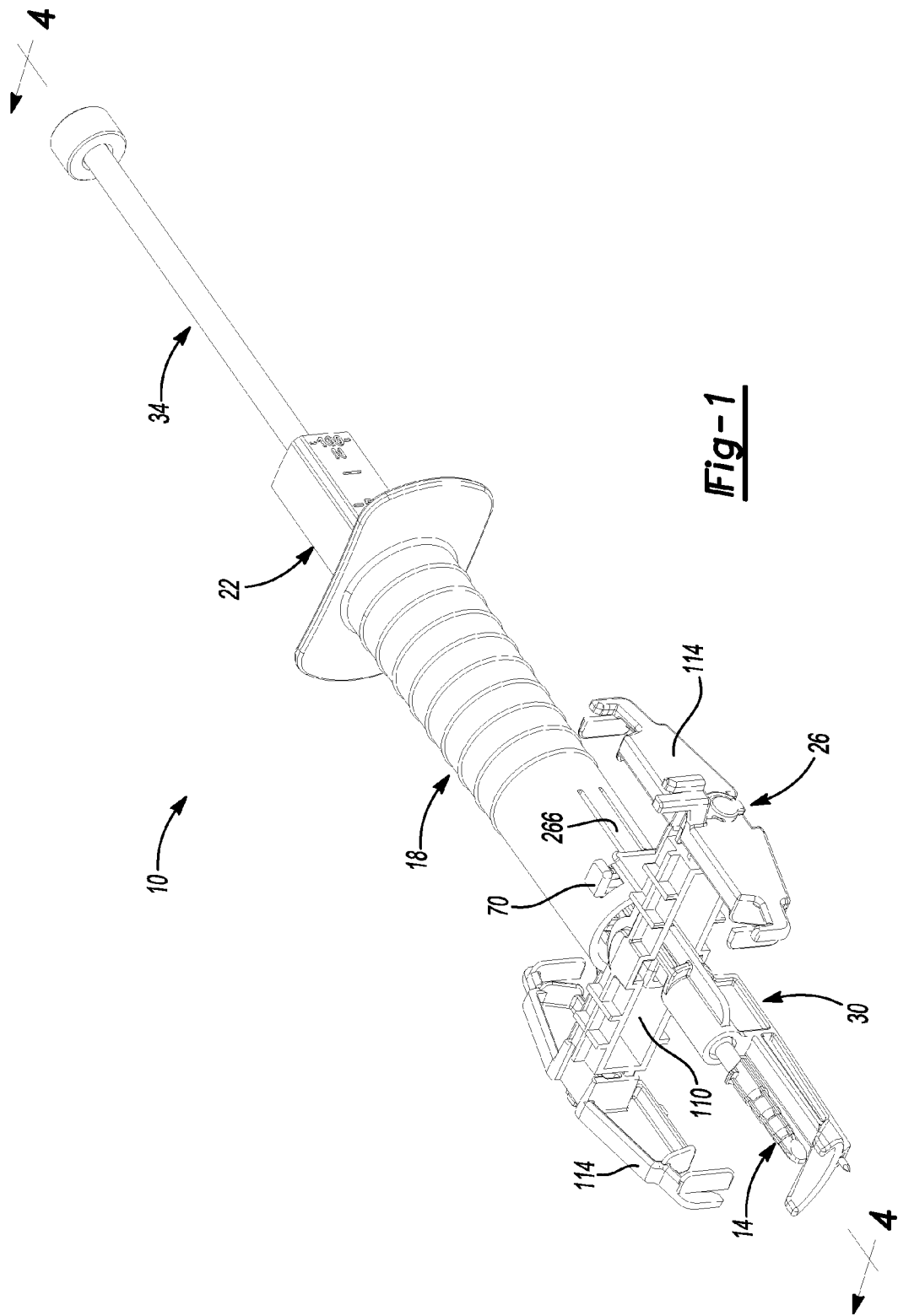

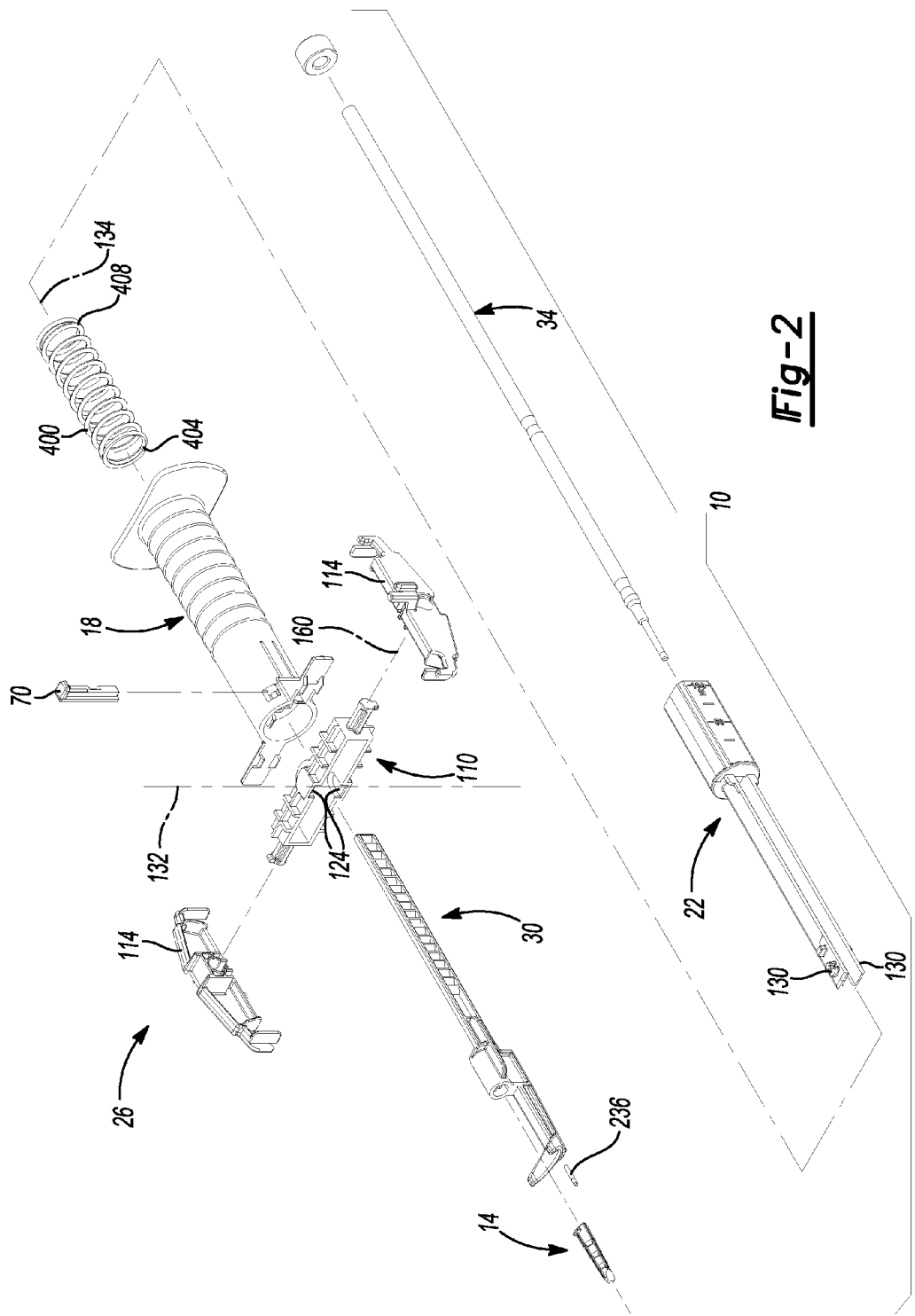

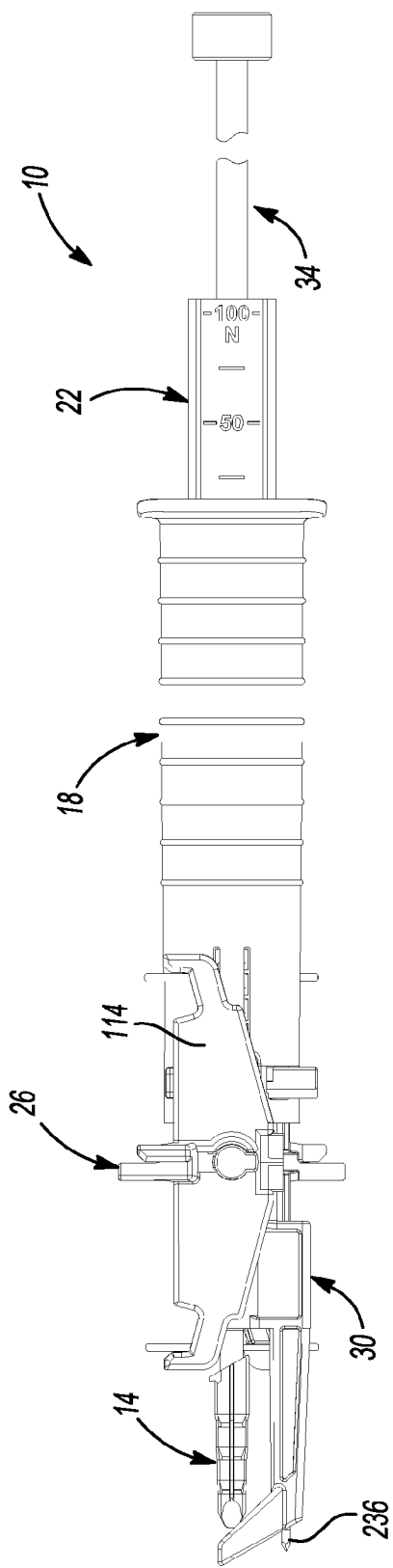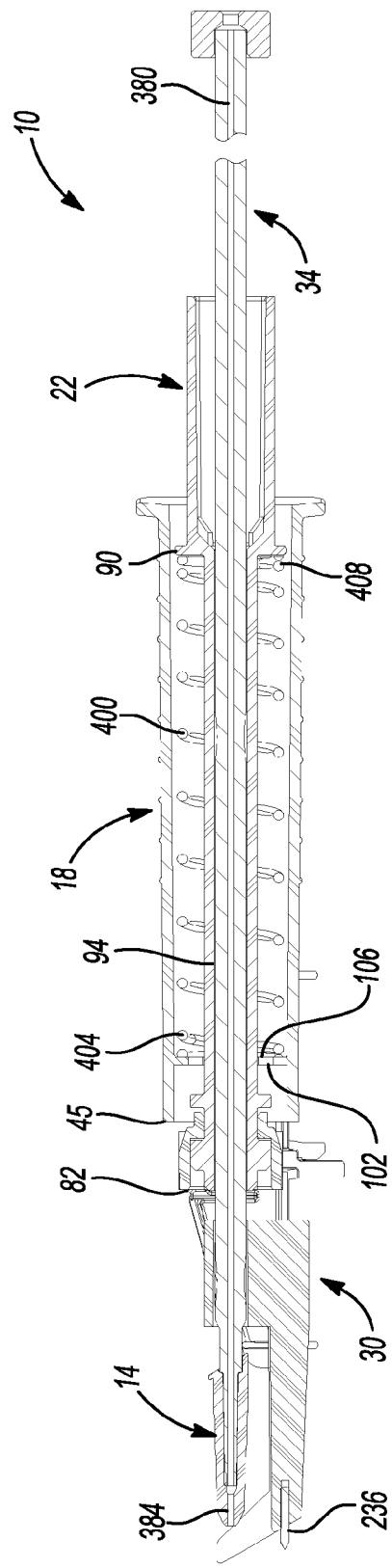

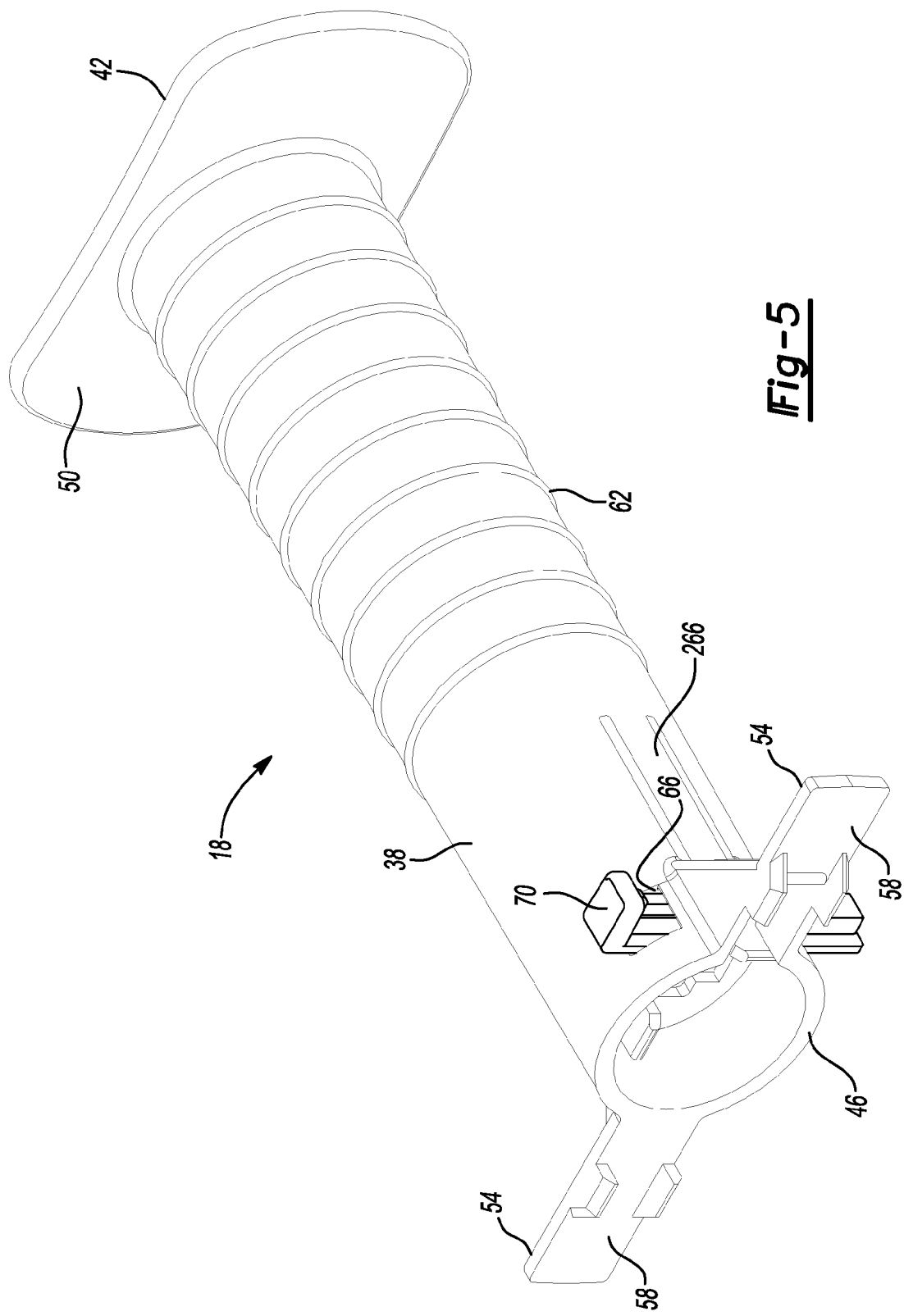

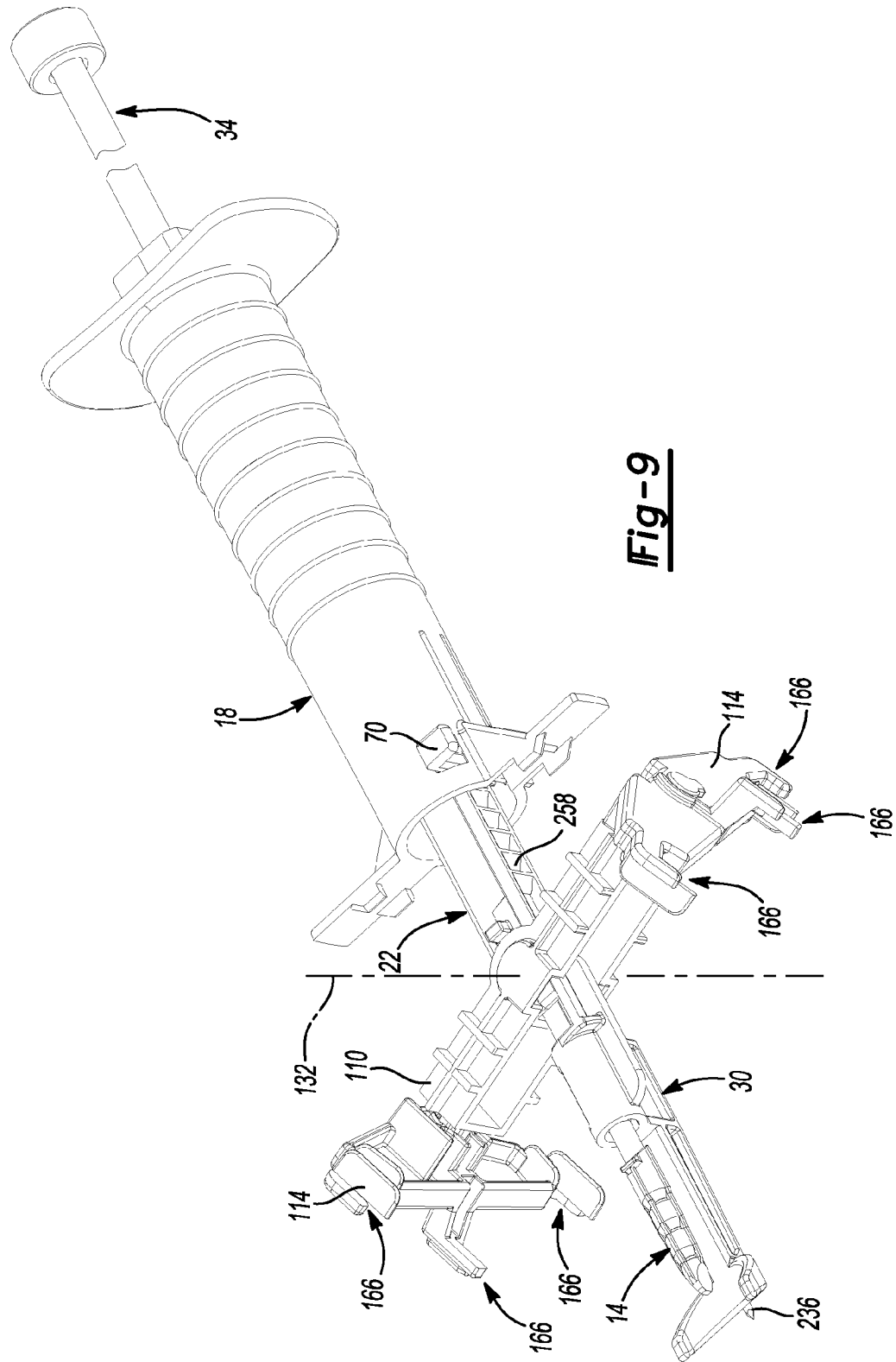

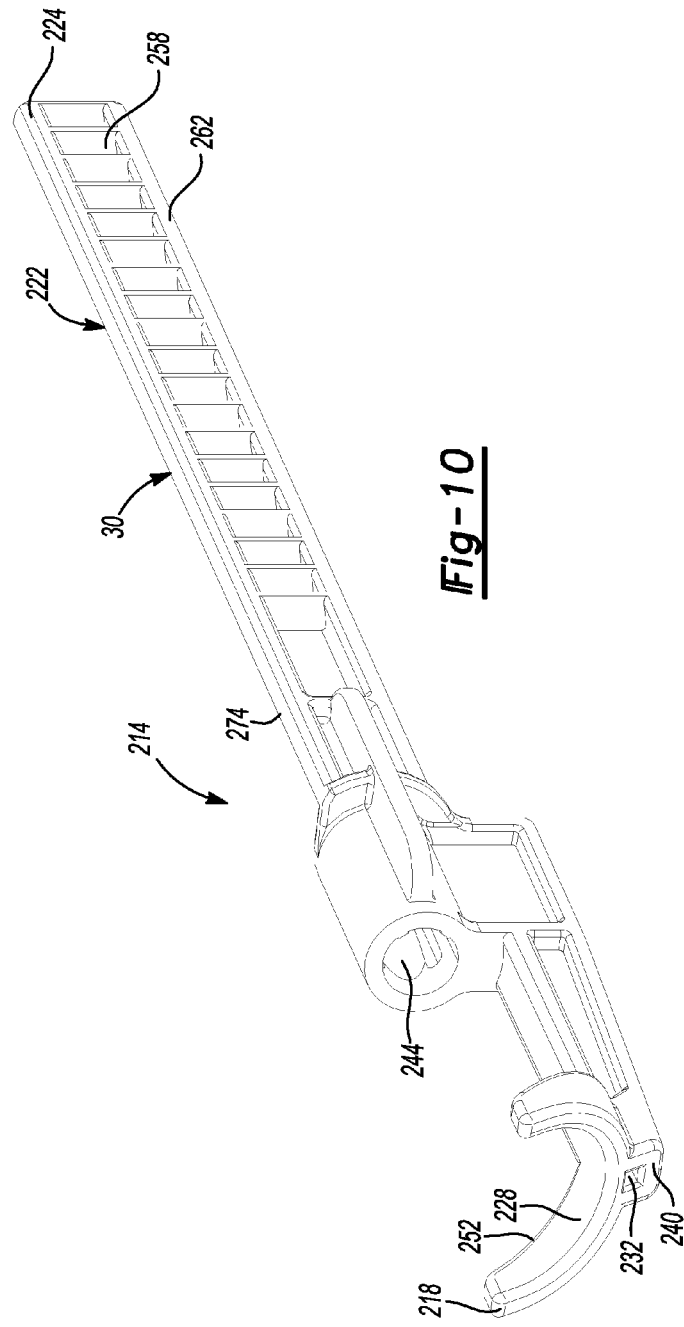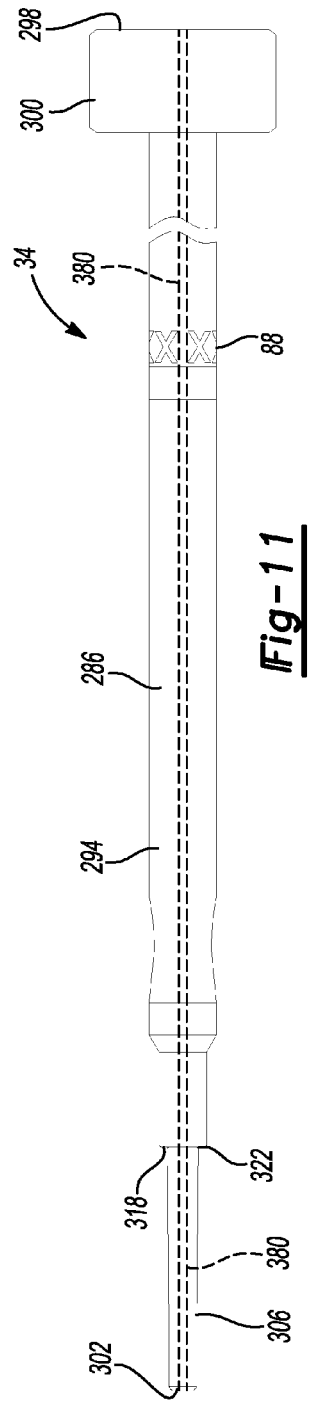

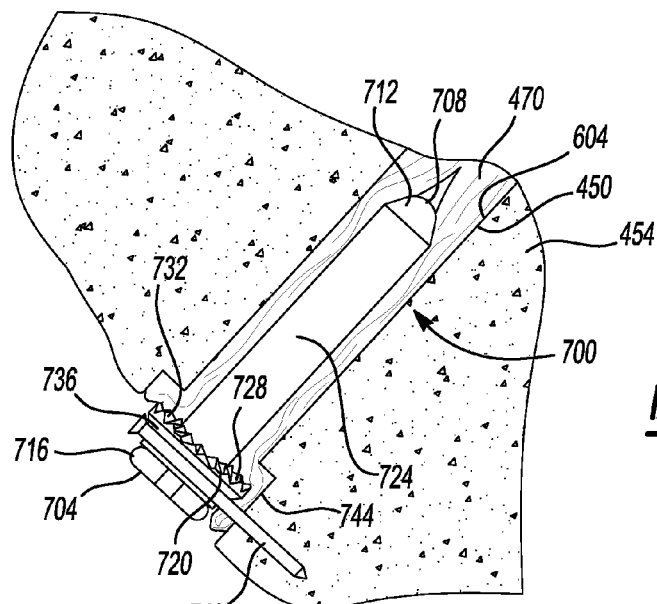
_Fig-17_
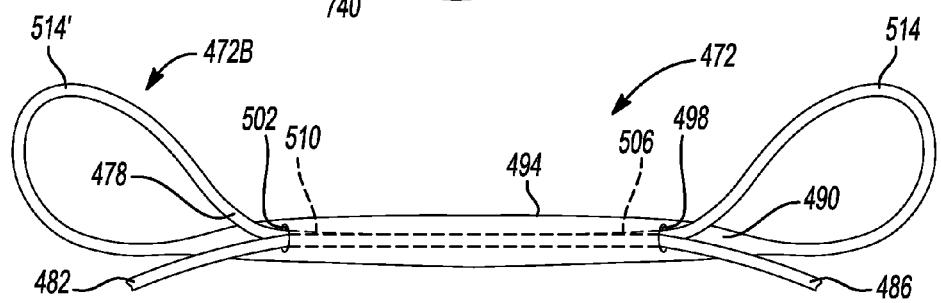
_Fig-18_
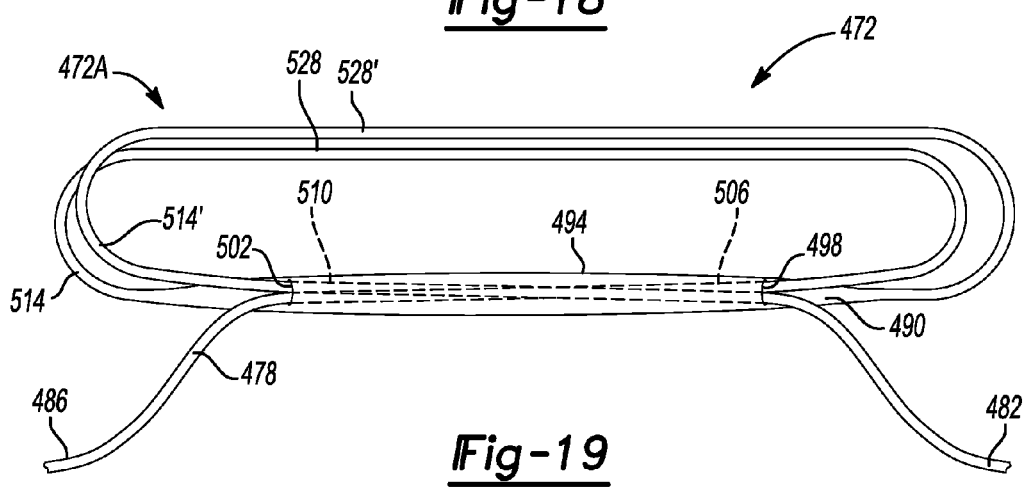
_Fig-19_

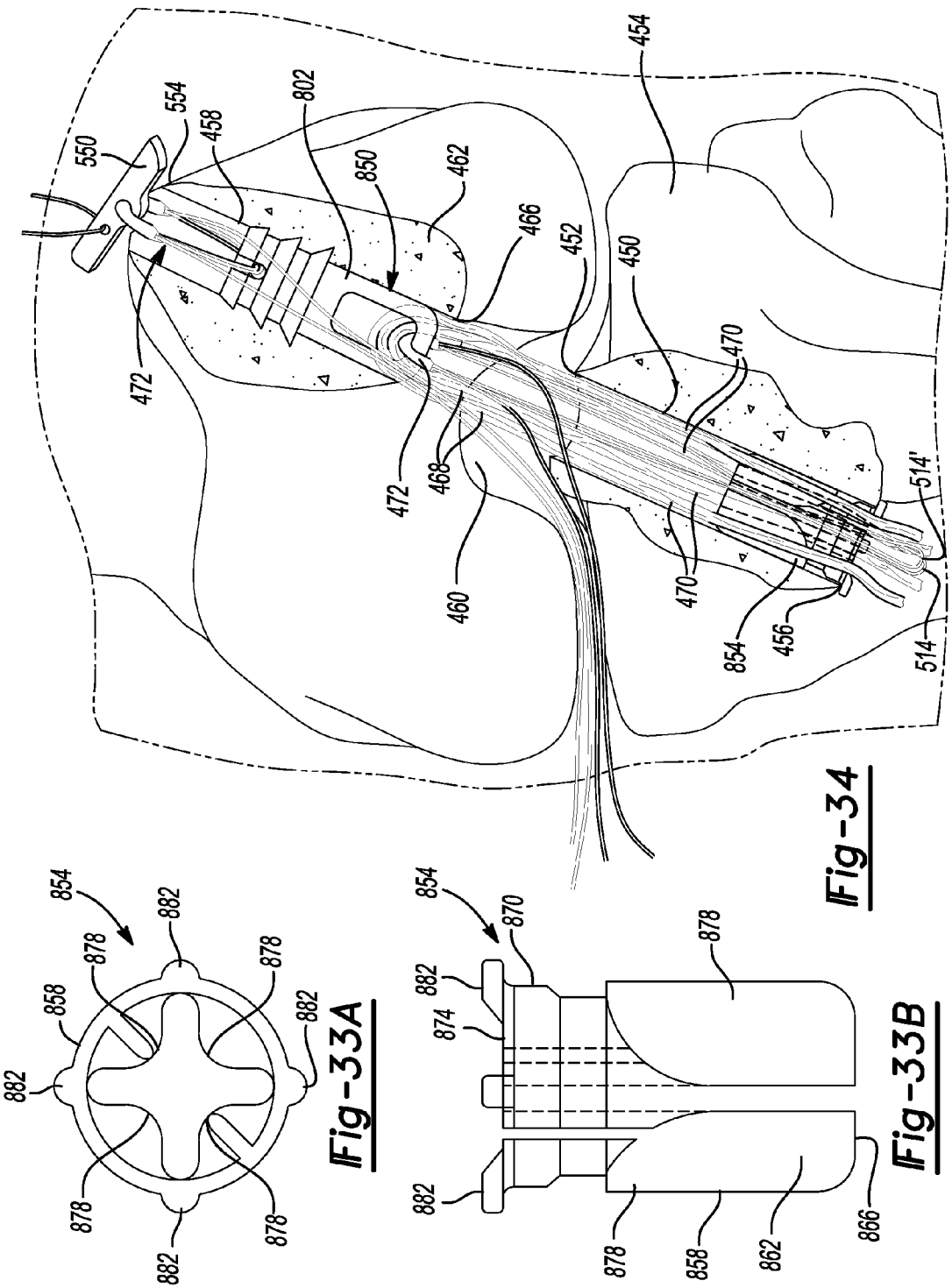

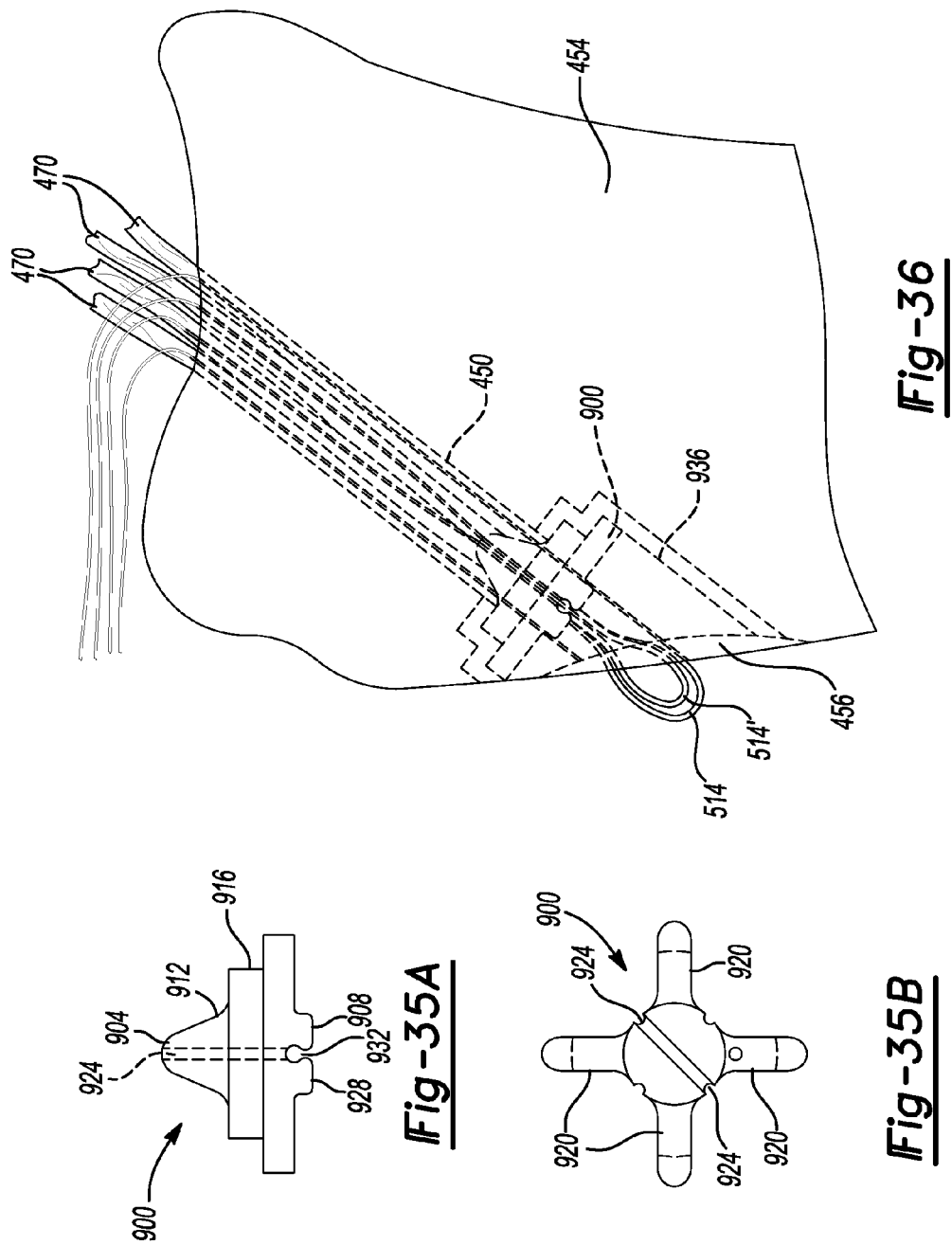

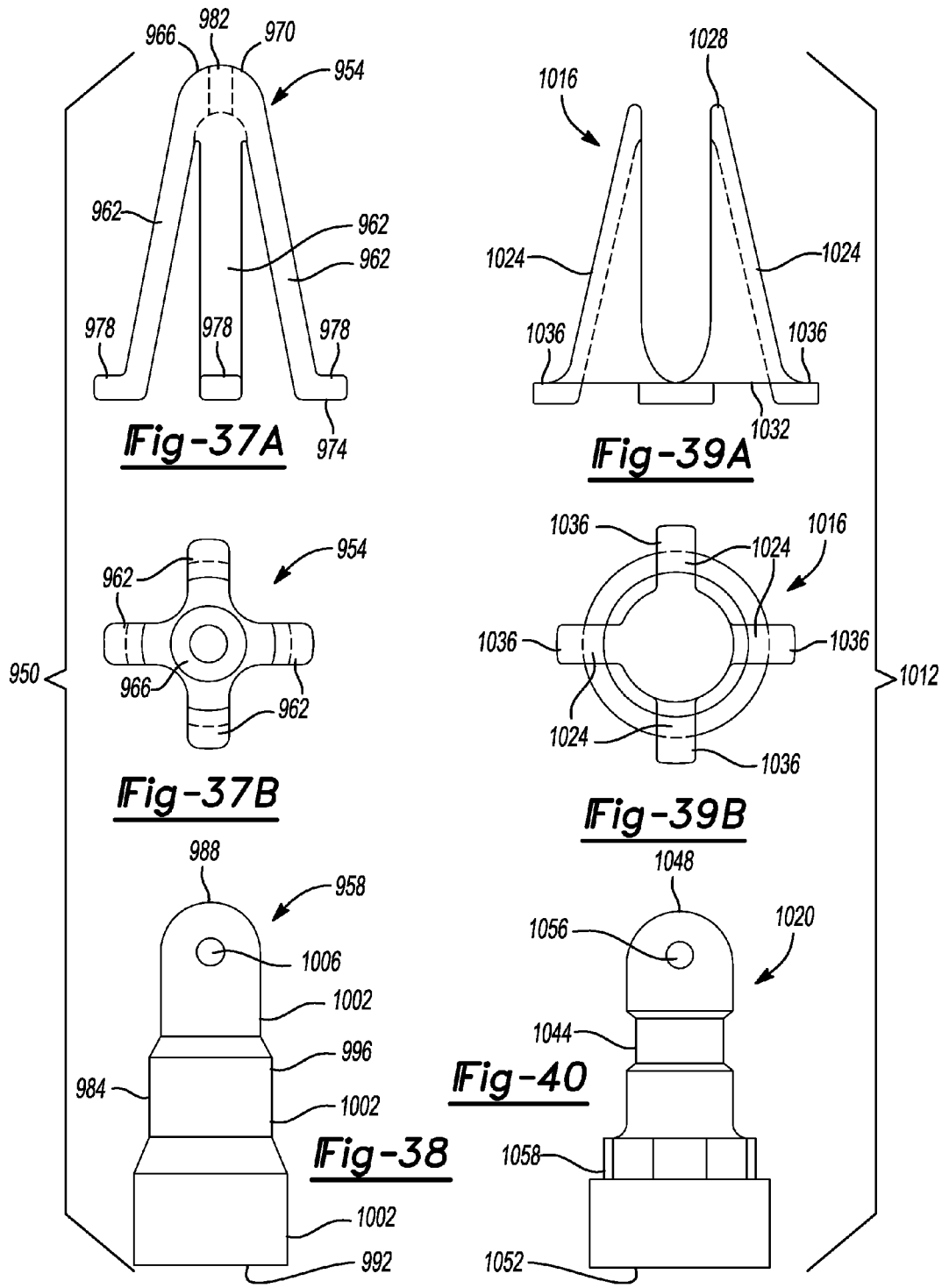

METHOD AND APPARATUS FOR TIBIAL FIXATION OF AN ACL GRAFT

CROSS REFERENCE TO RELATED APPLICATIONS

This application is related to U.S. patent application Ser. No. 13/109,672, entitled "Method and Apparatus for Fixation of an ACL Graft" and filed concurrently herewith and incorporated by reference herein.

FIELD

The present disclosure relates generally to a method and apparatus for fixation of an anterior cruciate ligament (ACL) graft.

BACKGROUND

This section provides background information related to the present disclosure that is not necessarily prior art.

Ligaments are strong fibrous connective soft tissue that connect the articular ends of bones to bind them together and to facilitate or limit motion. Injuries to ligaments are common, and patients who are physically active are generally more susceptible to such ligament injuries.

The anterior cruciate ligament (ACL) of the knee joint is a ligament frequently injured by such patients. Such injuries cause instability in the knee joint which, when left untreated, may lead to degenerative arthritis. Because of this condition, ACL reconstruction may be required. Generally during ACL reconstruction, a substitute soft tissue ligament or graft is attached to the femur and/or tibia to facilitate regrowth and permanent attachment. The substitute graft can include one or more graft bundles or strands that are tensioned prior to the femoral and/or tibial fixation.

SUMMARY

This section provides a general summary of the disclosure, and is not a comprehensive disclosure of its full scope or all of its features.

In one form, a tensioner system for use in tensioning graft strands in a knee reconstruction procedure is provided in accordance with various aspects of the present teachings. The tensioner system can include a handle assembly, a tensioner assembly coupled to the handle assembly and a drive shaft slidably received through and supported by the handle assembly. The tensioner assembly can include an arm support member rotatably coupled to the handle assembly and first and second arm members each rotatably coupled to lateral sides of the arm support member. Each arm member can include at least one graft attachment area adapted to be coupled to a graft strand. The arm support member can be configured to rotate about an axis perpendicular to a longitudinal axis of the tensioner system and perpendicular to an axis of rotation of each of the first and second arm members. The drive shaft can be received through and supported by the handle assembly such that proximal and distal ends of the drive shaft extend beyond respective proximal and distal ends of the handle assembly.

In another form, a method for use in graft fixation in a knee reconstruction procedure is provided in accordance with various aspects of the present teachings. The method can include forming a femoral tunnel in a femur and a tibial tunnel in a tibia, where the femoral tunnel has an opening adjacent a joint space between the femur and the tibia and the tibial tunnel has an entrance at the joint space and an opposite exit spaced apart from the joint space. The graft can be positioned into the femoral tunnel and retained relative to the femoral tunnel and passed though the tibial tunnel such that the graft extends beyond the exit of the tibial tunnel. The graft can be coupled to a tensioner device. A bone engaging member of the tensioner device can be positioned relative to the tibial tunnel. The graft can be tensioned by moving a portion of the tensioner device away from the bone engaging member thereby increasing a length of the tensioner device and applying tension to the graft strands. The method can also include ungrasping the tensioner device while the tensioner device maintains the tension in the graft.

In yet another form, a method for use in graft strand fixation in a knee reconstruction procedure is provided in accordance with various aspects of the present teachings. The method can include forming a femoral tunnel in a femur and a tibial tunnel in a tibia, where the femoral tunnel has an opening adjacent to a joint space between the femur and the tibia and the tibial tunnel has an entrance at the joint space and an opposite exit spaced apart from the joint space. A femoral fixation member coupled to a self-locking adjustable flexible member construct can be positioned into the femoral tunnel and the graft strands can be positioned around adjustable loops of the flexible member construct extending from the femoral tunnel. Free ends of the flexible member construct can be tensioned to reduce a size of the adjustable lops and draw the graft strands into the femoral tunnel, and the graft strands can be passed though the tibial tunnel such that the graft strands extend beyond the exit of the tibial tunnel. The graft strands can be coupled to first and second tensioning arms of a tensioner device, and a bone engaging foot of the tensioner device can be aligned relative to the tibial tunnel. The graft strands can be tensioned by moving an outer handle body of the tensioner device away from the tensioning arms, which can be allowed to rotate relative to the tensioner device and each other to provide substantially equal tension in each graft strand. The method can also include maintaining the tension in the graft strands with the tensioner device and engagement of the tensioner device to the tibia independent of any input from a user of the tensioner device. A drive shaft of the tensioner device can be translated relative to the tensioning arms and outer handle body to drive an implant into the tibial tunnel to fix the tensioned graft strands relative to the tibial tunnel.

In still another form, a method for use in graft strand fixation in a knee reconstruction procedure is provided in accordance with various aspects of the present teachings. The method can include forming a femoral tunnel in a femur and a tibial tunnel in a tibia, where the femoral tunnel has an opening adjacent a joint space between the femur and the tibia and the tibial tunnel has an entrance at the joint space and an opposite exit spaced apart from the joint space. The graft can be positioned into the femoral tunnel and retained relative to the femoral tunnel. The graft can be passed though the tibial tunnel such that the graft extends beyond the exit of the tibial tunnel, and the graft can be coupled to a tensioner device. A bone engaging member of the tensioner device can be positioned relative to the tibial tunnel. The tensioner device can be grasped and the graft can be tensioned by moving a handle body of the tensioner device away from the bone engaging member thereby increasing a length of the tensioner device and applying tension to the graft. The tensioner device can be used to maintain tension in the graft and alignment of a longitudinal axis of the tensioner device with a longitudinal axis of the tibial tunnel in an absence of an external force being applied to the tensioner device.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 1 is a perspective view of an exemplary graft strand tensioner having arms in a non-deployed position in accordance with the teachings of the present disclosure;

FIG. 2 is an exploded view of components of the tensioner of FIG. 1 in accordance with the teachings of the present disclosure;

FIG. 3 is a side view of the tensioner of FIG. 1 in accordance with the teachings of the present disclosure;

FIG. 4 is a sectional view of the tensioner of FIG. 1 in accordance with the teachings of the present disclosure;

FIG. 5 is a perspective view of an outer handle body of the tensioner having a tension release member in accordance with the teachings of the present disclosure;

FIG. 9 is a perspective view of the tensioner showing the ratcheting member in an advanced position and the tensioning member and arms in exemplary deployed or use positions in accordance with the teachings of the present disclosure;

FIG. 10 is a perspective view of a ratcheting member of the tensioner in accordance with the teachings of the present disclosure;

FIG. 11 is a side view of a driver shaft of the tensioner in accordance with the teachings of the present disclosure;

FIGS. 15-17 are perspective views of exemplary alternative implants for use with the tensioner in accordance with the teachings of the present disclosure;

FIGS. 18 and 19 depict exemplary adjustable knotless suture constructs that can be used in an ACL reconstruction procedure in accordance with the teachings of the present disclosure;

FIGS. 33A-34 are views depicting an implant for coupling a graft to the tibia and an associated exemplary ACL reconstruction procedure in accordance with the teachings of the present disclosure;

FIGS. 35A-36 are views depicting an implant for coupling a graft to the tibia and an associated exemplary ACL reconstruction procedure in accordance with the teachings of the present disclosure;

FIGS. 37A-40 are views depicting exemplary implants for coupling a graft to bone in an ACL reconstruction procedure in accordance with the teachings of the present disclosure.

DETAILED DESCRIPTION

Figure 6:
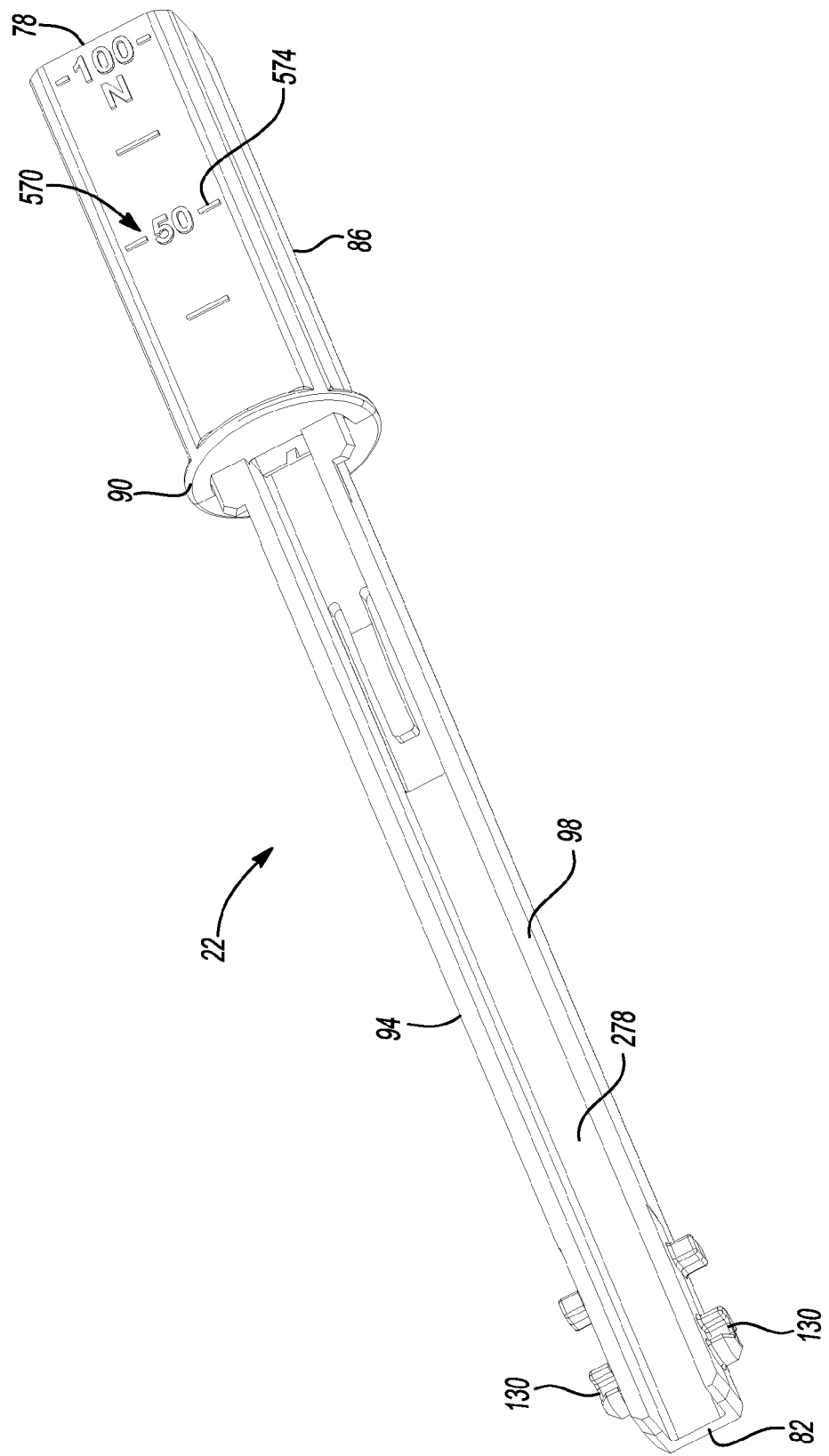
FIG. 6 is a perspective view of an inner handle body of the tensioner in accordance with the teachings of the present disclosure.

The following description is merely exemplary in nature and is not intended to limit the present disclosure, its application, or uses. It should be understood that throughout the drawings, corresponding reference numerals indicate like or corresponding parts and features. Throughout the description, exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Turning now to FIGS. 1-14 of the drawings, an exemplary tensioner 10 and an associated implant 14 are shown in accordance with the teachings of the present disclosure. As will be discussed in greater detail below, tensioner 10 and implant 14 can be used in connection with an ACL reconstruction procedure (e.g., FIGS. 20-28) where one or more looped graft bundles can be tensioned and coupled relative to a tibial tunnel. As will also be discussed below, in one exemplary configuration, a surgeon can operate tensioner 10 with one hand and tensioner 10 can provide equal or substantially equal tension to four graft strands extending from the tibial tunnel.

Tensioner 10 can be wholly disposable or reusable or partially disposable or reusable and can include an outer handle body 18, an inner handle body 22, a tensioning arm assembly 26, a ratcheting bone engaging member 30 and a driver shaft 34. Outer handle body 18 can include a hollow body 38 having a proximal end 42 and a distal end 46, as shown for example in FIG. 5. Proximal end 42 can include a flange 50 for use in supporting a surgeon or other user's hand and distal end 46 can include a pair of outwardly extending flanges 54 having arm engaging surfaces 58. Hollow body 38 can include a plurality of ribs or other protrusions 62 to aid the surgeon in gripping outer handle body 18. An aperture 66 can be formed in body 38 for receiving a tension release member 70, which will be discussed below in greater detail.

Inner handle body 22 can be received in outer handle body 18 and can include a proximal end 78 and a distal end 82, as shown for example in FIG. 6. Proximal end 78 can include a first portion 86 having a flange 90 formed on a distal end thereof and a second portion 94 having a C-shaped configuration 98 in cross section extending from flange 90 to distal end 82. As will be discussed in greater detail below, the C-shaped configuration 98 of second portion 94 can axially receive driver shaft 34 therein, as shown for example in FIG. 4. Outer handle body 18 can include an internal flange 102 having an aperture 106 sized and shaped to receive and support the inner handle body 22 and ratcheting member 30, as also shown in FIG. 4.

Figure 7:
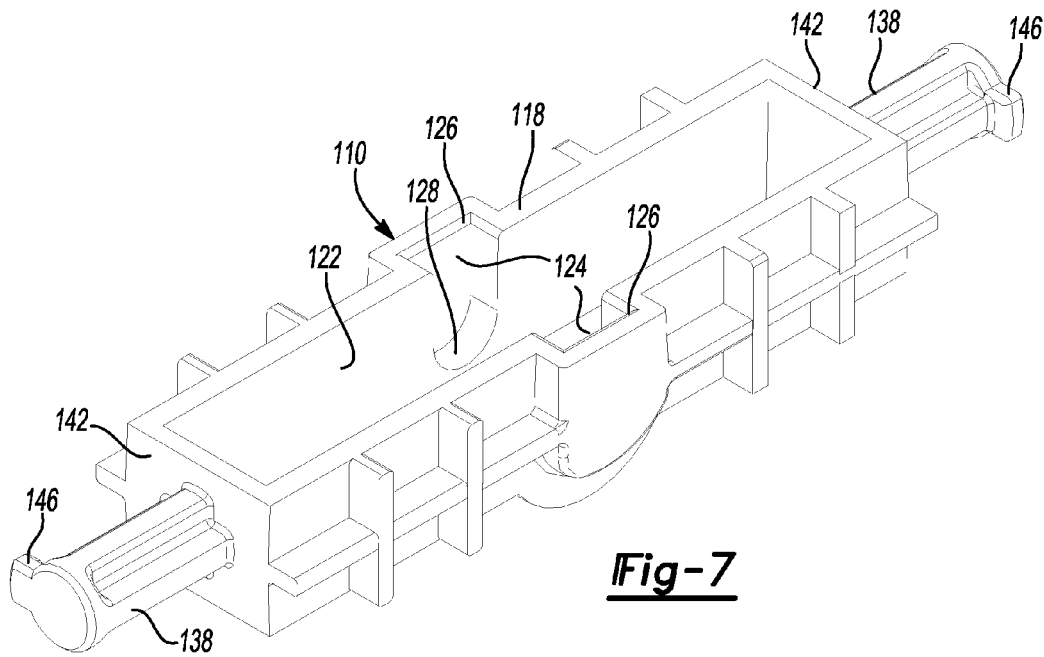
FIG. 7 is a perspective view of an arm support member of the tensioner in accordance with the teachings of the present disclosure.
Figure 8:
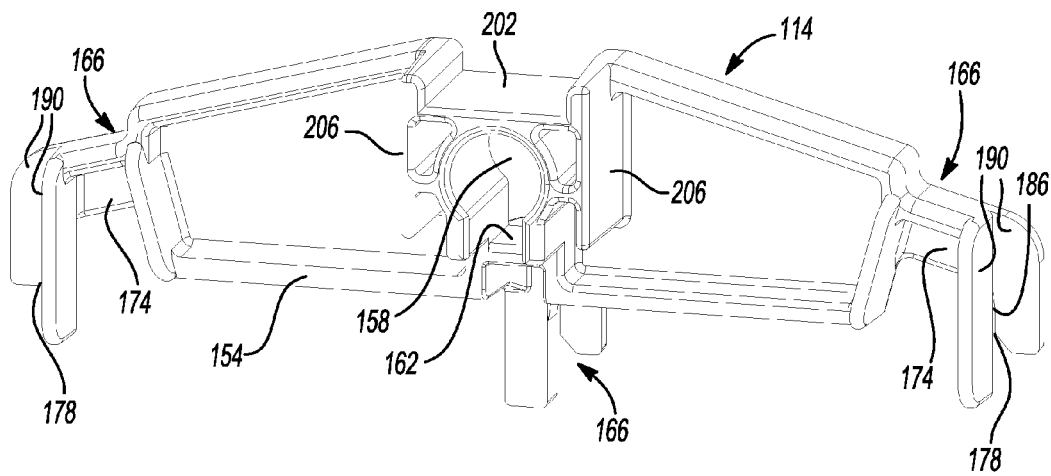
FIG. 8 is a perspective view of a tensioning arm of the tensioner in accordance with the teachings of the present disclosure.

Tensioning arm assembly 26 can include an arm support member 110 and a pair of tensioning arms 114, as shown for example in FIGS. 7 and 8 with reference to FIG. 2. Arm support member 110 can include a body 118 having a passage 122 therethrough and a pair of centrally positioned recesses 124 configured to receive a corresponding pair of projections 130 (FIG. 6) extending from distal end 82 of inner handle body 22. Each recess 124 can include an open end 126 and an arcuate shaped closed end 128. As will be discussed in greater detail below, arm support member 110 can rotate or pivot about an axis 132 perpendicular to a longitudinal axis 134 (FIG. 2) of tensioner 10 to cooperate with tensioning arms 114 to provide equal or substantially equal tension to graft strands that are coupled to tensioning arms 114. In the exemplary configuration illustrated, body 118 can have a rectangular shape with arm attachment members 138 extending from opposite lateral ends 142 thereof. Each arm attachment member 138 can include a flange or other retaining member 146 extending therefrom to retain the respective tensioning arm 114 thereon.

Each tensioning arm 114 can include a body portion 154 having a central aperture 158 configured to receive attachment member 138 for removably coupling tensioning arm 114 to arm support member 110. Each tensioning arm 114 can be rotatably coupled to a respective attachment member 138, where rotation of tensioning arms 114 about axis 160 aids in providing the equal or substantially equal tension to grafts strands coupled thereto. In other words, having arm support member 110 rotate about first axis 132 and tensioning arms 114 each rotate about second axis 160 allows each strand 470 (FIGS. 21 and 22) of the graft bundle to be separately tensioned and balanced. In the exemplary configuration illustrated, aperture 158 can include a recess 162 sized and shaped to receive retaining member 146 therethrough. Body portion 154 can include flexible member or suture attachment arrangements 166 at opposed longitudinal ends thereof to facilitate coupling the flexible member or suture 170 (e.g., FIG. 22) extending from a respective graft strand thereto, as will be discussed in greater detail below.

Briefly, however, each attachment arrangement 166 can include first and second attachment areas 174, 178 for use in securing the suture thereto. In one exemplary configuration, first attachment area 174 can be used to initially receive the suture 170, such as by wrapping the suture around the attachment area 174. The second attachment area 178 can include a slot 186 between adjacent flanges 190 sized and shaped to provide an interference fit to a suture received therein. In this regard, second attachment area 178 can be used to secure an end of suture 170 therein, as shown for example in FIG. 23. It should be appreciated however, that first and second attachment areas 174, 178 can be used individually or in combination to removably couple a respective suture 170 thereto. In another exemplary configuration, each arm 14 can include a third attachment arrangement 166 centrally positioned between the longitudinal ends, as shown for example in FIGS. 8 and 9. The third attachment arrangement 166 could be used, for example, with a graft bundle having an additional two ends.

Figure 22:
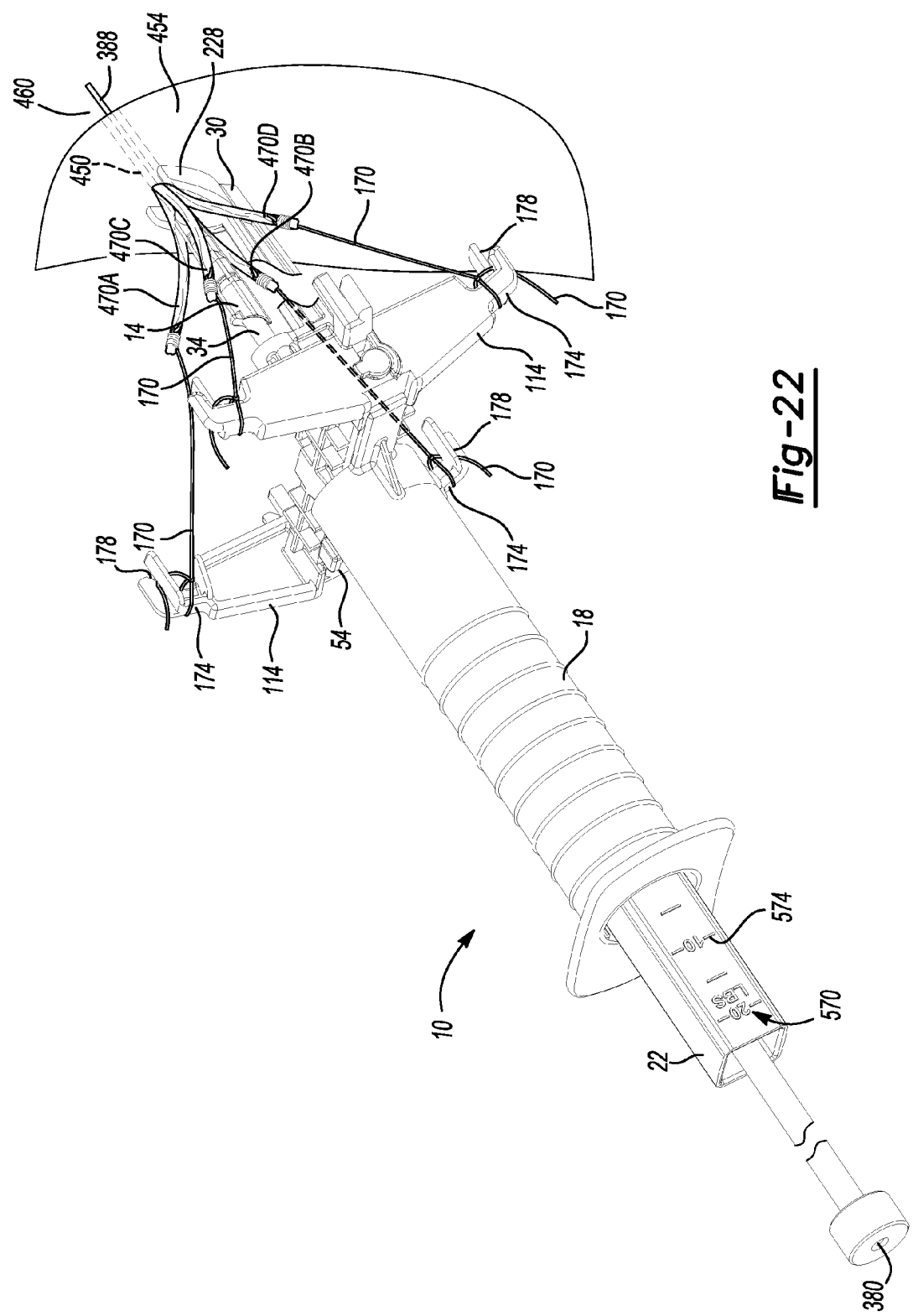

The tensioning arms 114 can also include first and second engagement surfaces 202, 206 configured to engage respective surfaces 58 of flanges 54 in the non-deployed and deployed positions of tensioning arms 114, as shown in FIG. 8 with reference to FIGS. 1 and 22. For example, one of second engagement surfaces 206 can engage respective surfaces 58 of flanges 54 when tensioning arms 114 are in the pre-use or non-deployed position, such as a shipping or storage position, as shown for example in FIG. 1. The tensioning arms 114 can be rotated to the initial use or deployed position where first engagement surfaces 202 of tensioning arms 114 engage respective surfaces 58 of flanges 54, as shown for example in FIG. 22.

The ratcheting member 30 can include a first portion 214 defining a distal end 218 and a second portion 222 extending therefrom and defining a proximal end 224, as shown for example in FIG. 10. First portion 214 can include a bone engaging member or foot 228 at the distal end 218 thereof and can include an aperture 232 for receiving a bone spike or other bone engaging or fixation member 236 (FIG. 2). Bone spike 236 can include a longitudinal length so as to extend beyond an outer surface 240 of distal end 218, as shown for example in FIG. 3. First portion 214 can also include a longitudinal aperture or throughbore 244 sized and shaped to receive driver shaft 34 therethrough, as will be discussed in greater detail below. In the exemplary configuration illustrated, bone engaging foot 228 can include a substantially U-shaped configuration 252 configured to align with a tibial tunnel and receive implant 14 and a portion of driver shaft 34 therethrough, as will also be discussed below in greater detail.

The second portion 222 can extend from the first portion 214 and can include ratchet teeth 258 along a longitudinal length of a first side 262 thereof. Ratchet teeth 258 can be configured to engage ratcheting pawl 266 (FIG. 5) formed in hollow body 38 of outer handle body 18. Ratcheting pawl 266 can be biased into engagement with ratchet teeth 258 when ratcheting member 30 is positioned in an assembled configuration within outer handle body 18, as will be discussed in greater detail below. The tension release member 70 can be in selective engagement with ratcheting pawl 266. In this regard, movement of tension release member 70 relative to aperture 66 and ratcheting pawl 266 can selectively disengage ratcheting pawl 266 from ratchet teeth 258 to release any tension imparted on associated graft strands coupled to tensioning arms 114, as will also be discussed in greater detail below.

The second portion 222 can include a second side 274 opposite first side 262, as shown for example in FIG. 10. Second side 274 can be configured to mate with an open end or side 278 of the C-shaped second portion 94 of inner handle body 22, as shown for example in FIG. 9 with reference to FIG. 6. Second side 274 can also include a longitudinally extending rib or protrusion configured to be received in the open end of the C-shaped second portion 222 to guide the ratcheting member 30 relative to inner handle body 22. In one exemplary configuration, the longitudinally extending protrusion can include an arcuate outer surface in cross-section configured to slidably engage an outer surface 286 (FIG. 11) of driver shaft 34 when the driver shaft 34 is received in inner handle body 22 in an assembled configuration of tensioner 10.

Driver shaft 34 can include a shaft body 294 extending from a proximal end 298 to a distal end 302, as shown for example in FIG. 11. In the exemplary configuration illustrated, proximal end 298 can include an impact or driver receiving member 300 secured thereto or integrally formed thereon. Distal end 302 can be configured to receive implant 14 thereon, as will be discussed below in greater detail. Briefly, however, distal end 302 can include an implant receiving portion 306 configured to be received in a bore 310 (FIG. 13) of implant 14. An open end of bore 310 can include a shoulder 314 configured to engage a corresponding shoulder 318 at a proximal end 322 of implant receiving portion 306. As will be discussed in greater detail below, driver shaft 34 can be impacted at proximal end 298 to drive implant 14 into a tibial tunnel, during which an impact force is transmitted from driver shaft 34 to implant 14 via engagement of corresponding shoulders 314, 318.

Figure 12:
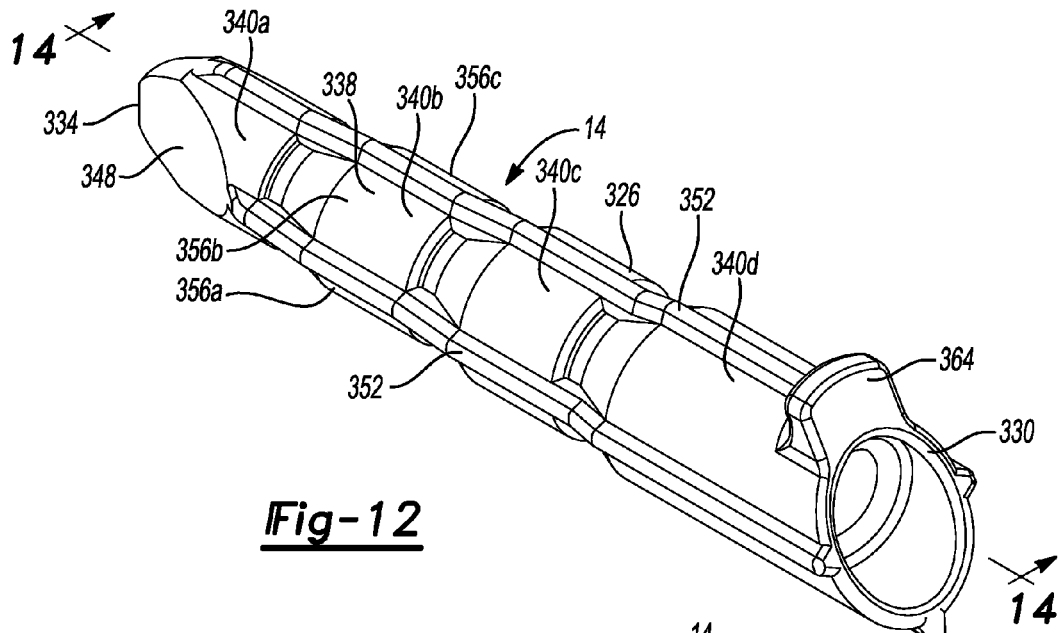
FIG. 12 is a perspective view of an exemplary implant for use with the tensioner in accordance with the teachings of the present disclosure.
Figure 13:
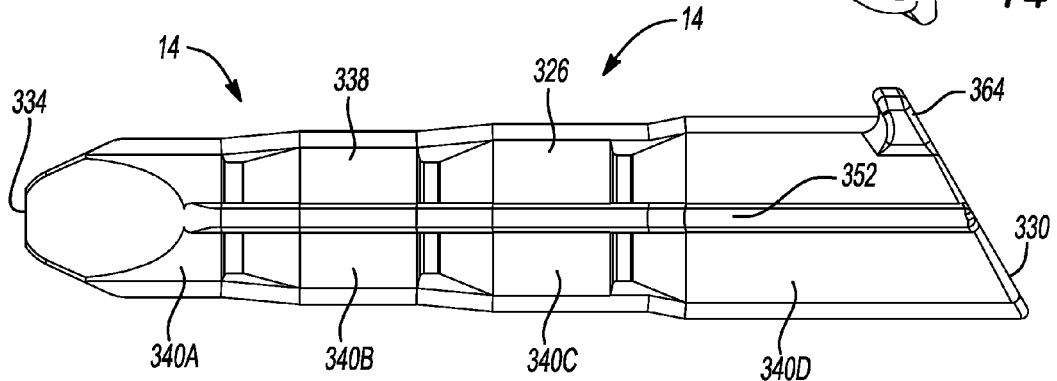
FIG. 13 is a side view of the implant of FIG. 12 in accordance with the teachings of the present disclosure.
Figure 14:
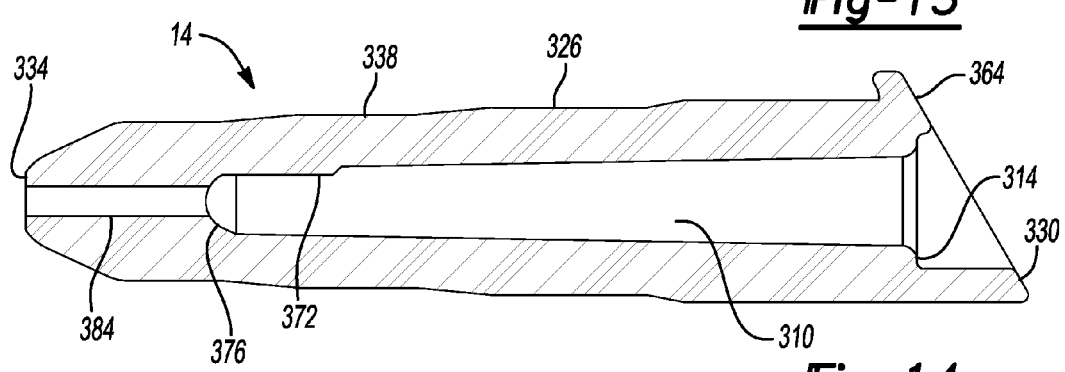
FIG. 14 is a sectional view of the implant of FIG. 13 in accordance with the teachings of the present disclosure.

Implant 14 can include body 326 having an open proximal end 330, a closed or substantially closed distal end 334, and the closed or substantially closed end bore 310 extending from proximal end 330 toward distal end 334, as shown for example in FIGS. 12-14. Body 326 can include an outer surface 338 having a plurality of annular portions or segments 340 of increasing outer diameter in a direction from the distal end 334 toward the proximal end 330. In the exemplary configuration illustrated, implant 14 can include four segmented sections 340A-340D, each having an increasing diameter as shown in FIG. 13. The distal end 334 can include a pair of opposed flattened sections 348 configured to aid in orientating the graft strands about implant 14, as will be discussed in greater detail below. In this regard, body 326 can also include four longitudinally and radially outwardly extending ribs 352 extending between the proximal and distal ends 330, 334 about outer surface 338. In the exemplary configuration illustrated, ribs 352 can be circumferentially spaced 90 degrees apart to divide outer surface 338 into four equally spaced quadrants 356A-356D configured to receive, in one exemplary configuration, four respective graft strands, as shown for example in FIG. 28.

Proximal end 330 of implant 14 can include a 45 degree angle relative to a longitudinal axis of the implant so as to mate in a substantially flush or otherwise substantially parallel manner with an outer surface of a tibia when implanted into a tibial tunnel formed at an approximate 45 degree angle to a longitudinal axis of the tibia. A protrusion 364 can extend from the proximal end 330 and can be configured to engage the outer surface of the tibia 454 to provide a tactile feel to the surgeon indicative of the implant 14 being driven an appropriate distance into the tibia and to prevent implant 14 from being driven too deeply into the tunnel, as shown for example in FIG. 26 with reference to FIG. 12. Bore 310 of implant 14 can include a reduced diameter portion 372 at a closed or substantially closed end 376 thereof that is sized and shaped to provide an interference fit with an end of the implant receiving portion 306 of driver shaft 34. The interference fit can aid in retaining implant 14 in a desired orientation relative to driver shaft 34 and the tibial tunnel during an ACL reconstruction procedure, as will be discussed below in greater detail.

In one exemplary configuration, driver shaft 34 can include a throughbore or cannulation 380 and implant 14 can include a throughbore 384 at a distal end thereof such that the bores 380, 384 are in alignment when implant 14 is received on driver shaft 34, as shown for example in FIGS. 4, 11 and 14. As will be discussed in greater detail below, the throughbores 380, 384 can receive a guidewire 388 (FIG. 25) for assisting in guiding implant 14 relative to the tibial tunnel 450.

With particular reference to FIGS. 1-4, an assembly configuration of tensioner 10 will now be discussed in greater detail. A spring 400 can be received over the second portion 94 of inner handle body 22 such that a proximal end 404 of spring 400 abuts flange 90. Inner handle body 22 can then be inserted into outer handle body 18 such that the distal end 82 of inner handle body 22 extends beyond the distal end 46 of outer handle body 18. Tension arm assembly 26 can be rotatably coupled to the distal end 46 of inner handle body 22 such that the recesses 124 of arm support member 110 engage the corresponding projections 130 of inner handle body 22. The second portion 94 of inner handle body 22 can include a length that cooperates with spring 400 such that a distal end 408 of spring 400 engages internal flange 102 of outer handle body 18 when tension arm assembly 26 is coupled to inner handle body 22, as discussed above. In this regard, spring 400 can exert a slight bias force against inner handle body 22, thereby urging inner handle body 22 proximally relative to outer handle body 18 until tension arm assembly 26 engages the distal end 46 of outer handle body 18.

In the exemplary configuration illustrated, one of the engagement surfaces 202, 206 of tensioning arms 114 can contact respective flanges 54 of outer handle body 18 under the bias force of spring 400 when the tensioner 10 is otherwise not in use. For example, when tensioning arms 114 are in the non-deployed or first position, as shown in FIG. 1, engagement surface 206 of tensioning arm 114 can engage flanges 54 and the bias force of spring 400 in cooperation with the mating engagement of surfaces 202 and flanges 54 can maintain the arms in the non-deployed position. Similarly, tensioning arms 114 can be rotated to the deployed or second position, as shown for example in FIG. 22, and can be maintained in this position by the bias force of spring 400 in cooperation with the mating engagement of surfaces 202 and flanges 54. For example, surface 202 can be orthogonal to surface 206, as shown in FIG. 7, such that when one or both tensioning arms 114 are rotated ninety degrees from the first position to the second position, the bias force of spring 400 in cooperation with the mating engagement of surface 202 and flanges 54 can maintain the tensioning arms 114 in the deployed or second position.

Ratcheting member 30 can be received through tension arm assembly 26 and into outer handle body 18 about the open end of C-shaped second portion 94 of inner handle body 22, as briefly discussed above. Drive shaft 34 can be received through proximal end 78 of inner handle body 22 such that it extends into and through C-shaped second portion 94 and throughbore 244 of ratcheting member 30, as shown for example in FIGS. 1, 2 and 4. Implant 14 can be coupled to implant receiving portion 306 of driver shaft 34. It should be appreciated that the order or sequence of assembled components of tensioner 10 discussed above is merely exemplary and other assembly sequences are possible and contemplated herein.

With additional reference to FIGS. 18-28, operation of tensioner 10 will now be discussed in greater detail in connection with an exemplary ACL reconstruction procedure. The exemplary ACL reconstruction procedure will make reference to a first or tibial tunnel 450 formed or drilled into a tibia 454 and a second or femoral tunnel 458 formed or drilled into a femur 462, as shown for example in FIG. 20. The tibial tunnel 450 can include a first end or entrance 452 and a second end or exit 456 opposite of a joint space 460 between the femoral and tibial tunnels. Similarly, femoral tunnel 458 can include a first end or entrance 466 adjacent joint space 460 and can include a second end or exit 474, or can be formed as a blind tunnel. In one exemplary configuration, the tibial tunnel 450 can be formed at about a 45 degree angle to a longitudinal axis of the tibia, as is also known in the art. The tunnels 450, 458 can be formed in any appropriate manner, such as those generally known in the art, and will not be described in further detail herein.

Figure 20:
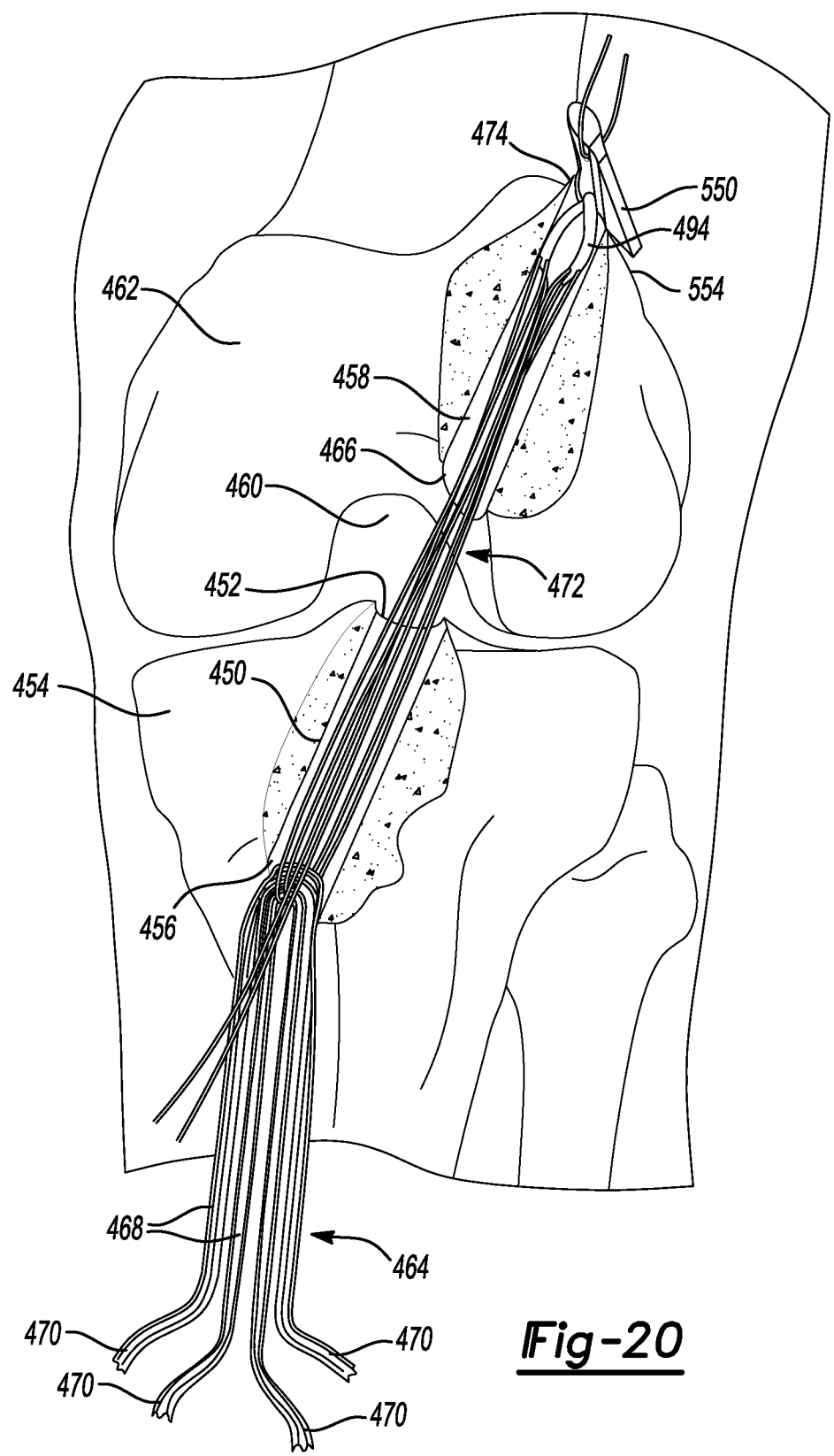
FIGS. 20-24 depict coupling a graft to a femur and tibia in an exemplary ACL reconstruction procedure in accordance with the teachings of the present disclosure.
Figure 21:
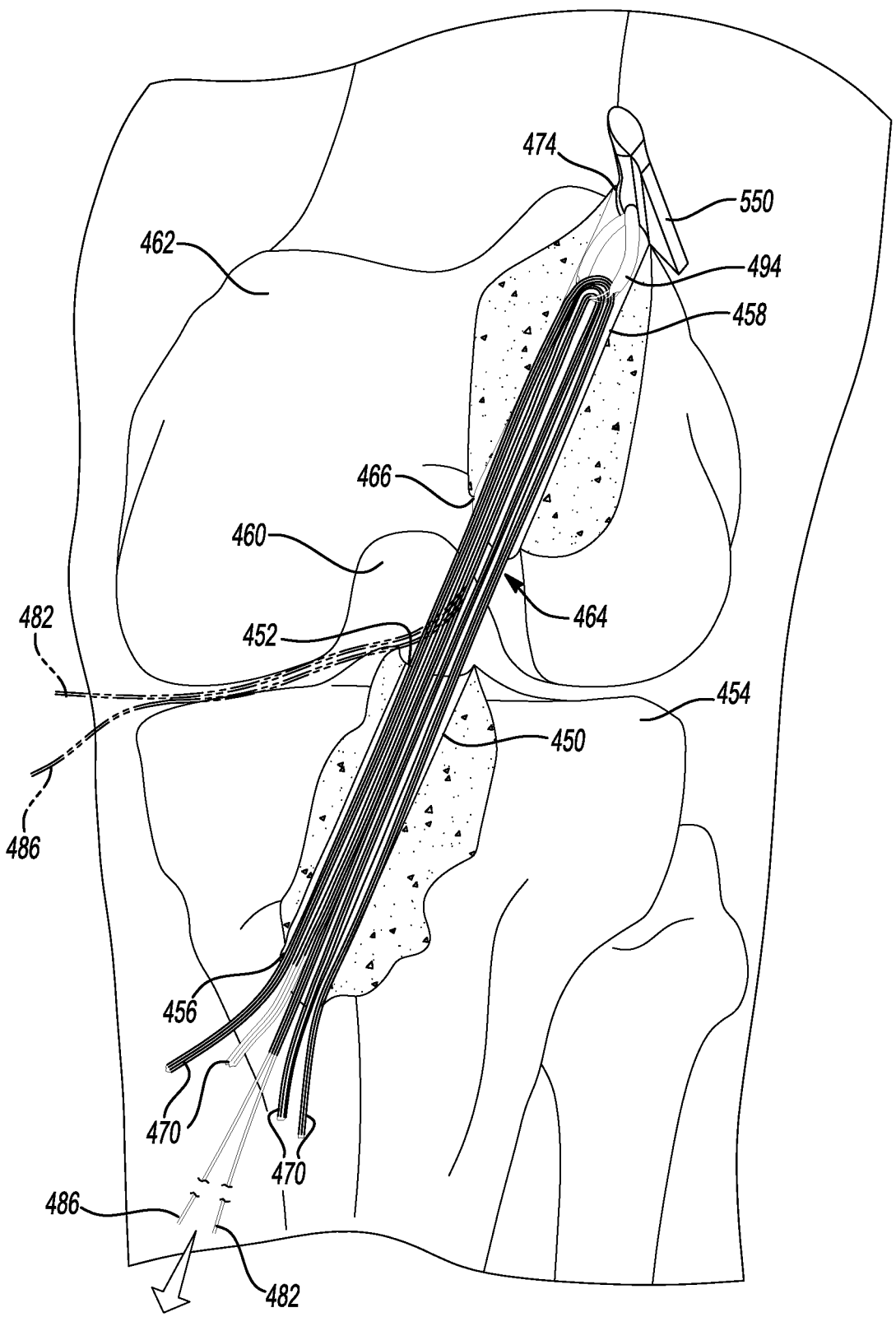

Once the tunnels 450, 458 are formed, a natural or artificial graft loop or bundle 464 can be passed through the tibial tunnel 450 and into the femoral tunnel 458 as shown for example in FIGS. 20 and 21. In the exemplary configuration, the graft bundle 464 can include two graft loops 468 looped around an adjustable self-locking flexible member or suture construct 472 (FIGS. 18 and 19). The two graft loops 468 can thus include four graft strands 470 extending from an exemplary flexible member construct 472, as shown for example in FIG. 20. It should be appreciated that while the discussion continues with reference to two graft loops and four graft strands, various other graft configurations can be used, including more or less graft loops and/or individual graft strands secured together at one end. In one exemplary aspect, graft 464 can include a synthetic or natural graft, such as an autograft or an allograft.

Adjustable self-locking flexible member construct 472 can include a double loop configuration 472A shown in FIG. 19 or a bowtie loop configuration 472B shown in FIG. 18. With particular reference to FIG. 18, adjustable flexible member construct 472B can include a hollow flexible member or suture 478 having a first end 482 and a second end 486, and can include a body 490 that defines a longitudinal passage portion 494 therein between first and second ends 482, 486. The passage portion 494 can define a pair of apertures 498, 502 at opposed ends thereof. To form construct 472B, the first end 482 can be passed through aperture 498 and passage portion 494 and out aperture 502 such that a portion 506 of flexible member 478 following first end 482 extends through passage portion 494. In a similar manner, second end 486 can be passed through aperture 502 and passage portion 494 and out aperture 498 such that a portion 510 of flexible member 478 following second end 486 also extends through passage portion 494. This configuration forms two loops 514 and 514', as shown in FIG. 18. It should be appreciated that each of the first and second ends 482, 486 can alternatively be pushed through a respective space defined between adjacent individual fibers of the braided flexible member 478 such that the respective spaces defined between fibers comprise apertures 498, 502 in communication with an interior longitudinal passage.

The pulling or tensioning of ends 482, 486 can cause movement of portions 506, 510 relative to passage portion 494, and the loops 514, 514' can be reduced to a desired size or placed in a desired tension. Tension in loops 514, 514' can cause the body 490 defining the passage portion 494 to be placed in tension and therefore cause passage portion 494 to constrict about portions 506, 510 passed therethrough. This constriction reduces the diameter of passage portion 494, thus forming a mechanical interface between the exterior surfaces of portions 506, 510 and an interior surface of passage portion 494. This constriction results in static friction between the interior and exterior surfaces at the mechanical interface, causing the adjustable flexible member 478 to "automatically" lock in a reduced size or diameter configuration in which tension is maintained. Flexible member construct 472B with adjustable loops 514, 514' can be used to position and tension a replacement graft, such as in an ACL reconstruction procedure, as will be discussed herein.

With reference to FIG. 19 and continuing reference to FIG. 18, adjustable flexible member construct 472A can be formed to include a double loop configuration having two loops 514, 514' that each traverse a path from one end of passage portion 494 to the other end thereof, instead of each loop being disposed at respective opposite ends of passage portion 494 as in construct 472B. Flexible member construct 472A can be formed by passing the first end 482 of the flexible member through aperture 502, through passage portion 494 and out aperture 498. The second end 486 can be passed through aperture 498, through the passage portion 494 and out the aperture 502. In various aspects, the first and second apertures 498, 502 can be formed during the braiding process as loose portions between pairs of fibers defining the flexible member 478, as discussed above. Passing ends 482, 486 through the apertures 498, 502 can form the loops 514, 514'. The loops 514, 514' can define mount or summit portions 528, 528' of the adjustable flexible member construct 472A and can be disposed generally opposite from the passage portion 494. Flexible member construct 472A with adjustable loops 514, 514' can be similarly used to position and tension a replacement graft, such as in the ACL reconstruction procedure.

The longitudinal and parallel placement of the first and second ends 482, 486 of the flexible member 478 within the passage portion 494 resists the reverse relative movement of the first and second portions 506, 510 of the flexible member construct 472 once it is tightened. The tensioning of the ends 482, 486 can cause relative translation of the portions 506, 510 relative to passage portion 494. Upon applying tension to the first and second ends 482, 486, the loops 514, 514' can be reduced to a desired size or placed in a desired tension. Tension in the loops 514, 514' can cause the body of the flexible member 478 defining the passage portion 494 to be placed in tension and therefore cause passage portion 494 to constrict about the portions 506, 510 similarly to the constriction discussed above with respect to construct 472B. This constriction can cause the adjustable flexible member construct 472A to "automatically" lock in a reduced size or smaller diameter configuration without the use of a knot. A further discussion of the flexible member constructs 472 is provided in U.S. patent Ser. No. 11/541,506 filed on Sep. 29, 2006 entitled "Method and Apparatus for Forming a Self-Locking Adjustable Suture Loop" assigned to Biomet Sports Medicine, LLC, now U.S. Pat. No. 7,601,165, and the disclosure of which is incorporated by reference herein.

With reference to FIG. 20, passage portion 494 of flexible member construct 472 can be coupled to a femoral fixation member, such as a fixation member 550, to facilitate femoral fixation or retention of graft 464 relative to femoral tunnel 458. The fixation member 550 can be, for example, a product sold by Biomet Sports Medicine, LLC under the name ToggleLoc™. A further discussion of the fixation member 550 can be found in U.S. Pat. No. 7,601,165. Fixation member 550 with construct 472 coupled thereto can be passed through the tibial and femoral tunnels 450, 458 and coupled to an outer surface 554 of femur 462, as shown in FIG. 20. Fixation member 550 can be sized and shaped to include a first profile that allows insertion through the tibial and femoral tunnels 450, 458, and a second profile that allows engagement with a positive locking surface upon rotation outside of the femoral tunnel 458. It should be appreciated that other apparatus and associated techniques can be used for femoral fixation in connection with an ACL reconstruction procedure, such as for example a femoral cross pin with the blind femoral tunnel and/or those discussed below in connection with one or more of FIGS. 29-40.

At this point, graft 464 can be passed through the loops of construct 472 extending from tibial tunnel 450. Tensioning of the first and second ends 482, 486 applies tension to the loops, thus pulling the graft 464 into the tibial and femoral tunnels 450, 458, as shown in FIG. 21. In this regard, the first and second ends 482, 486 can extend through the tibial and femoral tunnels 450, 458 and then be tensioned. In this configuration, the ends 482, 486 can then be removed from the tibial tunnel 450 such that they exit through the joint space 460, as shown in FIG. 21. Alternatively, the ends 482, 486 can extend only through the femoral tunnel 458 and then through the joint space 460 before they are subsequently tensioned. In the exemplary configuration shown in FIG. 21, the loops of construct 472 can be fully tensioned to draw graft 464 up to passage portion 494. In an alternative exemplary configuration, the loops can be tensioned to draw graft 464 into the femoral tunnel and proximate passage portion 494, while stopping short of fully tensioning the loops to thereby provide for further tensioning of the loops after tibial fixation of the graft has occurred, as will be discussed below in greater detail.

With particular reference to FIGS. 22-27, tensioning and tibial fixation of graft 464 with tensioner 10 will now be discussed in greater detail. After coupling graft 464 to femur 462 with member 550, the four strands 470 can extend through and exit the tibial tunnel 450, as shown in FIG. 22. At this point, tensioner 10 can be positioned or aligned with the tibial tunnel 450 such that the foot 228 of ratcheting member 30 is approximately parallel to an adjacent surface of the tibia, as also shown in FIG. 22. As discussed above, the foot 228 can include a forty-five degree angle relative to the longitudinal axis 134 of tensioner 10 so as to align the tensioner longitudinal axis 134 with an axis of the tibial tunnel 450, which can also be formed at a forty-five degree angle relative to a longitudinal axis of the tibia 454. It should be appreciated that other angles can be used for the foot 28 and tunnel 450. In one exemplary configuration, the guidewire 388 can be inserted into the tibial tunnel such that one end extends into the joint space 460 and the other end extends from an opposite end 456 of the tibial tunnel 450. In this configuration, the tensioner 10 can be aligned with the tibia 454 such that the guidewire 388 is received into throughbore 380 of driver shaft 34. The guidewire 388 can include a predetermined length so as to not extend to the proximal end 298 of driver shaft 34.

The tensioning arms 114 can be rotated from the first non-deployed position shown in FIG. 1 to the second deployed position shown in FIG. 22 in anticipation of coupling the graft strands 470 thereto. It should be appreciated that tensioning arms 114 can be placed in the deployed position before or after aligning the tensioner 10 with the tibial tunnel 450. Similarly, the graft strands 470 can be coupled to the tensioning arms 114 before or after aligning tensioner 10 relative to tibial tunnel 450. Each graft strand 470 can be coupled to a respective attachment arrangement 166 at the longitudinal ends of each tensioning arm 114. In this regard, each arm can be coupled to two graft strands 470 via suture or flexible member 170 coupled to the respective graft strands, as shown in FIG. 22. At this point, the tensioning arms 114 can be engaged with outer body flanges 54, as also shown in FIG. 22.

Figure 23:
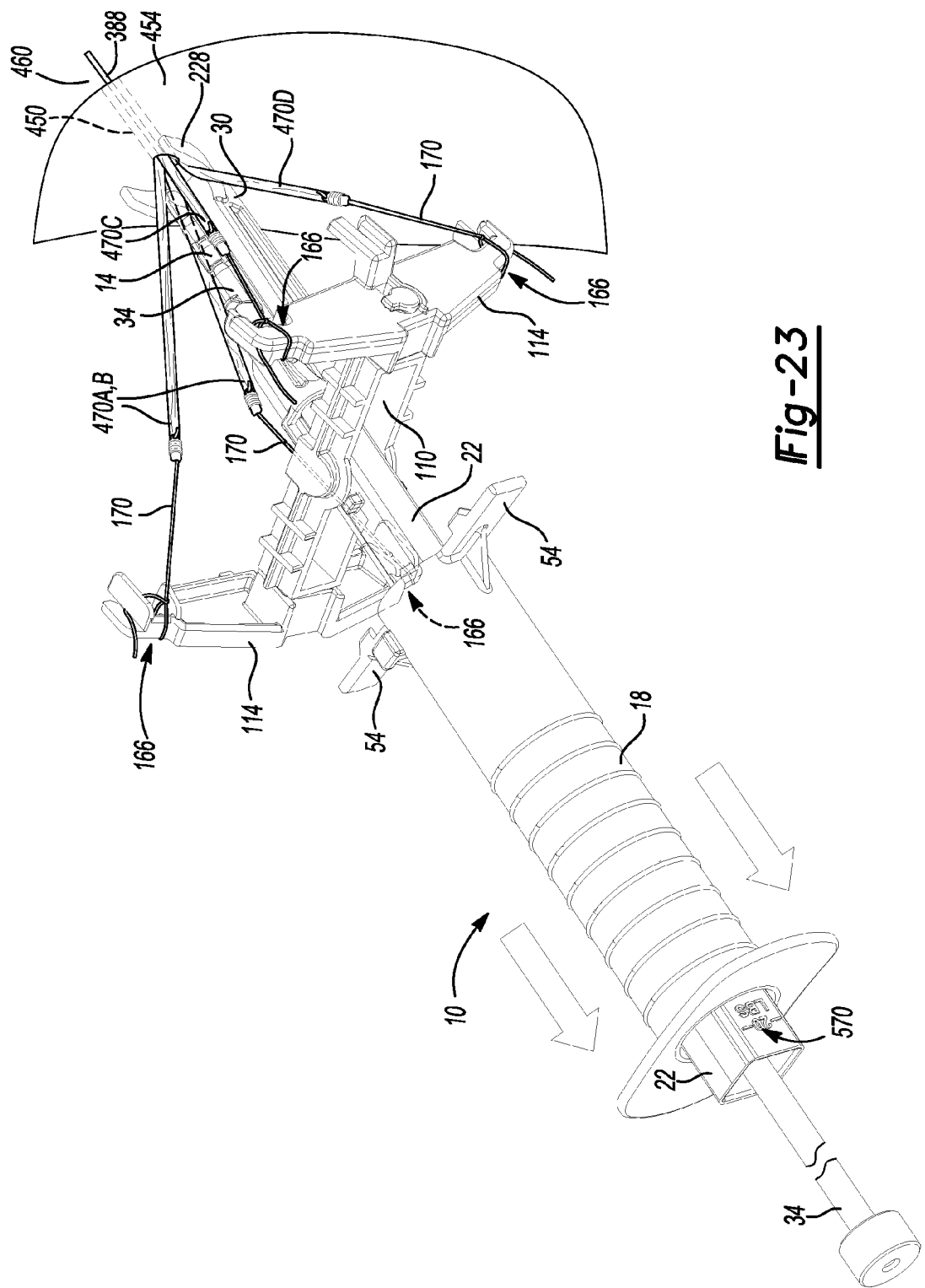

To tension graft strands 470 a first time, the surgeon can apply a force to the outer handle body 18, such as by pulling with one hand against flange 50, to compress spring 400 between flanges 102 and 90 and move the outer handle body 18 relative to the inner handle body 22 and ratcheting member 30, as shown for example in FIG. 23. As the tension arm assembly 26 is coupled to the inner handle body 22 and the graft strands 470, compressing spring 400 by moving outer handle body away from the tibia exerts a force on the inner handle body 22 toward the tibia thereby pushing the ratcheting member 30 incrementally toward the tibia 454. This action increases a longitudinal length of the overall tensioner 10 and thus applies an increasing amount of tension to graft strands 470 by moving tensioning arms 114 farther away from tibial tunnel 450. As outer handle body 18 is moved to apply tension to strands 470, ratchet pawl 266 engages the ratchet teeth 258 to maintain a desired position of outer handle body 18 relative to the ratcheting member 30 and thus maintain the desired tension. In addition, as tension is applied to the graft strands 470 with tensioner 10, bone spike 236 can engage the tibia 454 to aid in maintaining the position of tensioner 10 with tibial tunnel 450 during the ACL reconstruction procedure. In this regard, the tensioner 10 can stay in place relative to the tibial tunnel and tibia when under tension and thus does not require a user to hold or otherwise support tensioner 10 to maintain its position relative to the tibia when under tension.

The first portion 86 of inner handle body 22 can also include a scale 570 having indicia 574 indicative of an amount of tension being imparted onto graft strands 470 by operation of tensioner 10 as shown for example in FIGS. 9, 22 and 23. In this regard, spring 400 can be calibrated relative to scale indicia 574 such that as outer handle body 18 is moved relative to inner handle body 22 to tension the graft strands 470, the flange 50 can align with a particular indicia 574 to indicate an amount of tension being placed on graft strands 470.

As tension is applied to graft strands 470 as discussed above, tension arm assembly 26 moves away from the distal end of outer handle body 18, as shown in FIG. 23. At this point, arm support member 110 can now rotate about axis 162 relative to inner handle body 22, as also shown in FIG. 23. Allowing arm support member 110 to rotate relative to inner handle body 22 in cooperation with allowing tensioning arms 114 to individually rotate about axis 160 relative to arm support member 110 provides for being able to apply equal tension to each of graft strands 470. In this regard, the rotating capabilities of arm support member 110 and arms tensioning 114 can compensate for differences in length of individual graft strands 470 and/or the accompanying attachment sutures to balance the tension in each graft strand. With this compensation capability, the surgeon or clinician does not have to ensure that each graft strand 470 and accompanying suture exiting the tibial tunnel 450 has the same length from the tunnel 450 to the tensioner 10.

Once tension is applied to the graft strands 470 as discussed above, the tensioner 10 can maintain the tension of strands 470 until released via actuation of tension release member 70. In this regard, upon tensioning graft strands 470 with tensioner 10, the tensioner can remain secured to the tibia 454 and aligned with the tibial tunnel 450 without the aid of the surgeon or clinician continuing to hold the tensioner 10. With this capability of tensioner 10, the surgeon can, for example, cycle the knee joint to remove any laxity from the tensioned graft while the tensioner essentially self-maintains its position relative to the tibia 454 and tibial tunnel 450. If such cycling of the joint results in a decrease of tension on the graft strands 470, the surgeon can again pull or move outer handle body relative to inner handle body to tension the graft strands 470 a second time to increase the tension on strands 470 to the desired amount.

With the desired tension being applied to the graft strands by tensioner 10 and the knee joint being optionally cycled as discussed above, the implant 14 can be implanted into the tibial tunnel 450 to secure the tensioned graft strands 470 to the tibia 454, as will be discussed in greater detail below. It should be appreciated that by securing the grafts strands 470 about the horizontally and vertically spaced apart four attachment arrangements 166 of the tension arm assembly 26, the graft strands 470 are effectively separated into four quadrants at the exit of the tibial tunnel 450 corresponding to the four quadrants 356A-356D of implant 14 as shown for example in illustrative FIG. 28.

Implant 14 can then be advanced by translating driver shaft 34 relative to the inner and outer handle bodies 18, 22 and the ratcheting member 30 such that implant 14 is proximate the entrance of tibial tunnel 450. The opposed flattened sections 348 at the distal end of implant 14 can aid in separating the graft strands 470 upon implantation such that two strands 470A, 470B are on one side of the implant 14 and the other two strands 470C and 470D are on the opposite side of the implant 14 as shown for example in illustrative FIG. 28. The longitudinal ribs 352 can aid in further separating the strands 470 upon implantation such that each strand 470A-470D is positioned in a respective quadrant 356A-356D. It should be appreciated that while strands 470A-470D have been discussed above as correlating to quadrants 356A-356D, strands 470A-470D can be placed in different quadrants 356A-356D so long as one strand is in each quadrant 356A-356D.

Figure 24:
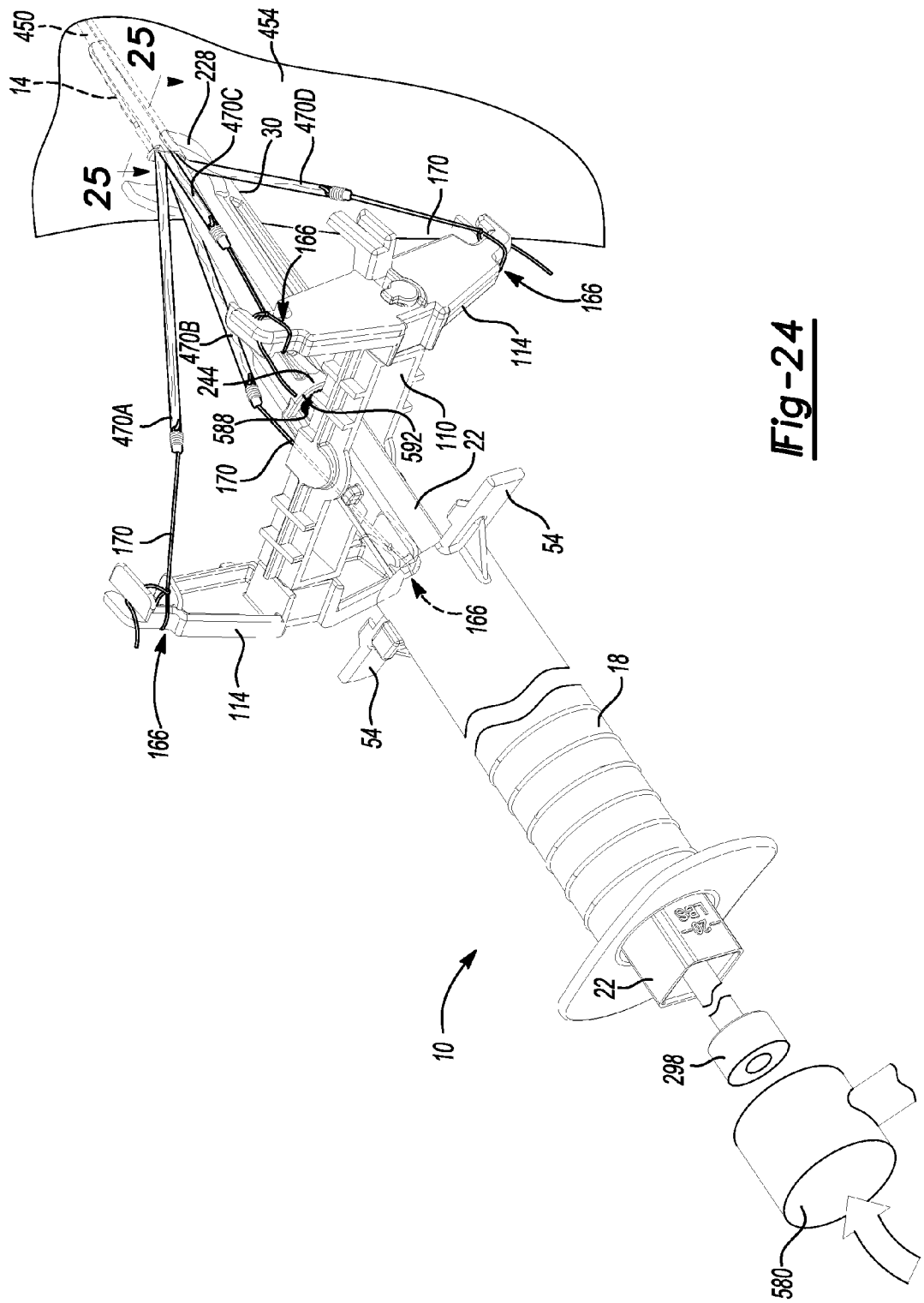

A driving or impacting instrument 580 can be used to impart a driving force on the proximal end 298 and translate driver shaft 34 relative to the outer and inner handle bodies 18, 22 and ratcheting member 30 along the axis of the tibial tunnel 450. Such translation of driver shaft 34 can drive implant 14 into tibial bone tunnel 450 about graft strands 470A-470D to fix graft 464 relative to the tibia 454, as shown in FIG. 24 with reference to FIGS. 25-27. Implant 14 can be driven axially into the tibial tunnel 450 until protrusion 364 extending from the proximal end 330 thereof engages an adjacent outer surface of the tibia 454. Protrusion 364 can serve as a stop and/or provide a tactile feel to the surgeon that implant 14 has been driven to the desired depth. In an exemplary configuration, driver shaft 34 can also include indicia, such as an indicator band 588, to provide an additional indication of the desired drive depth. In this configuration, the indicator band 588 can be adjacent a proximal end 592 of the throughbore 244, as shown for example in FIG. 24.

Figure 25:
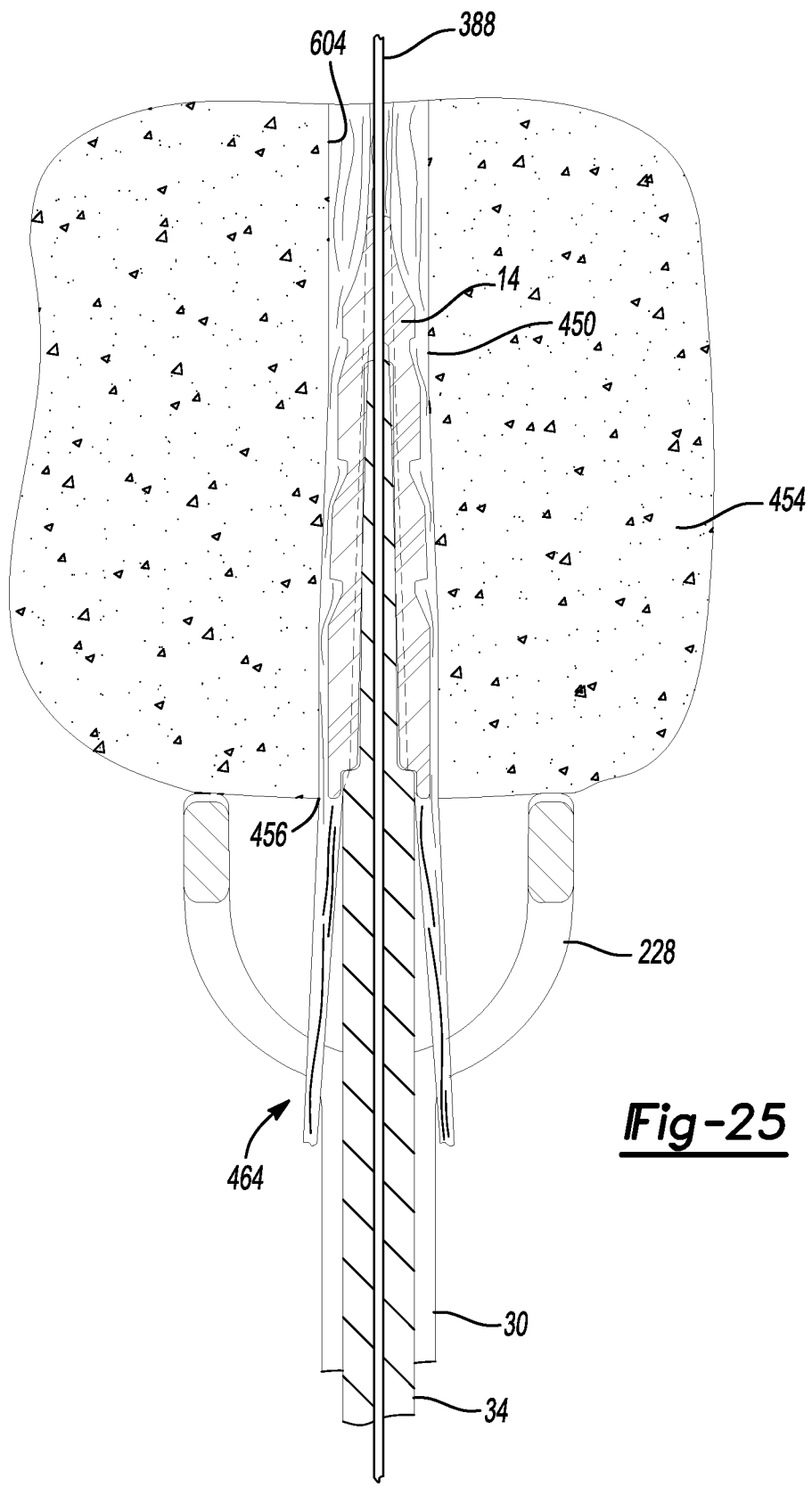
FIG. 25 depicts a partial section view of an exemplary implant securing graft strands to the tibia in accordance with the teachings of the present disclosure.
Figure 26:
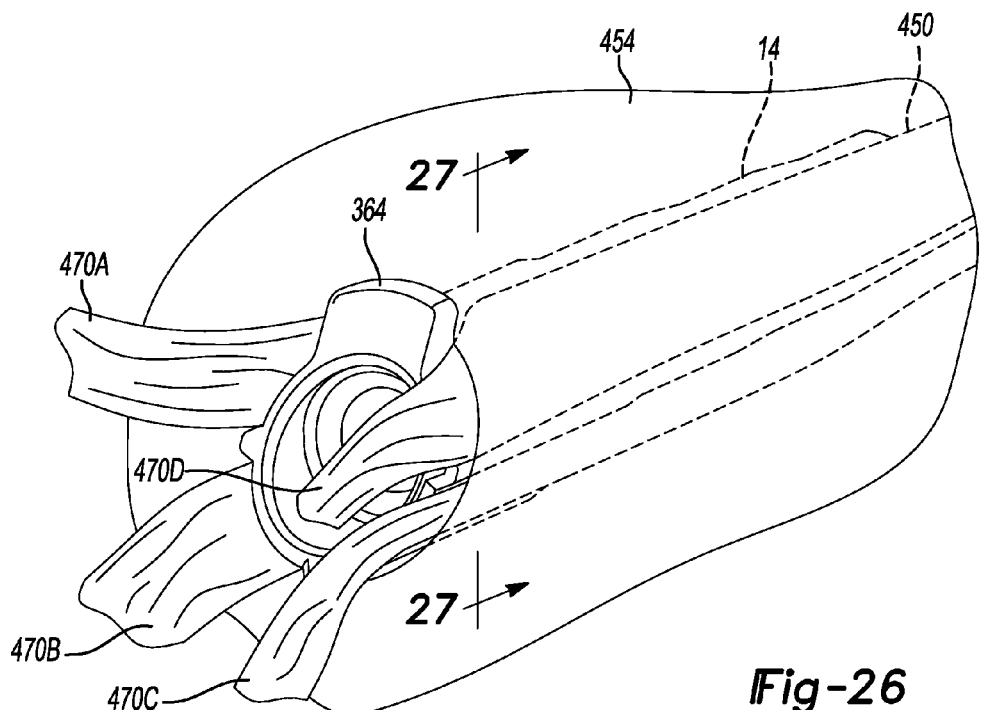
FIG. 26 depicts a partial perspective view of an implant coupling four grafts strands to the tibia in accordance with the teachings of the present disclosure.
Figure 27:
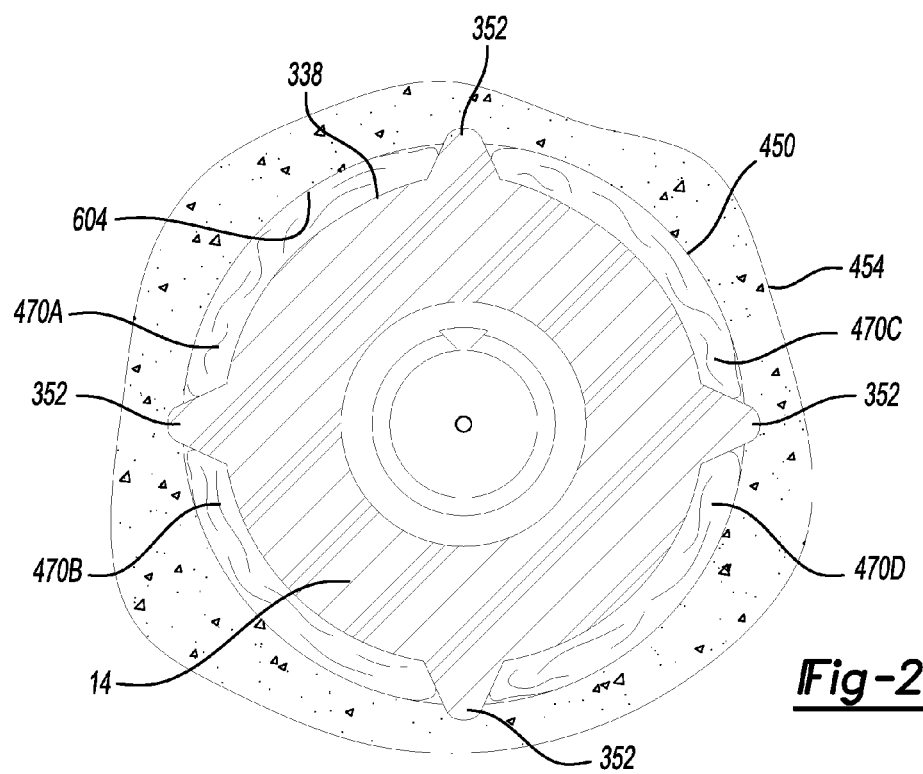
FIG. 27 depicts a sectional view of FIG. 26 in accordance with the teachings of the present disclosure.
Figure 28:
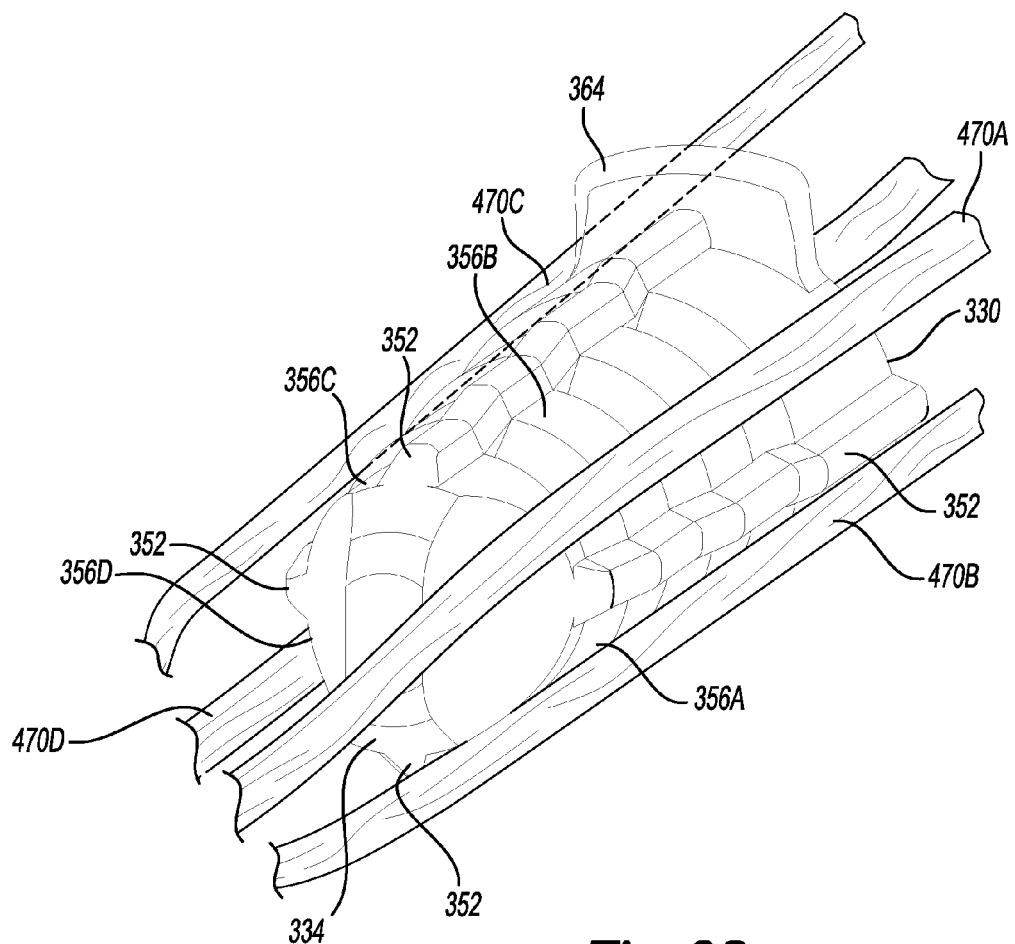
FIG. 28 is a perspective view illustrating an exemplary placement of four graft strands about the implant with the tibial tunnel removed in accordance with the teachings of the present disclosure.

As the implant 14 is driven into the tibial bone tunnel, implant 14 can compress the graft strands between an outer surface 338 of implant 14 and an inner surface or wall 604 of the tibial tunnel 450, as shown for example in FIGS. 25 and 27. In one exemplary configuration shown in FIG. 25, implant 14 can compress each graft strand 470A-470D to substantially fill an area between adjacent longitudinal ribs 352 and the inner surface 604 of the tibial tunnel 450 and the outer surface 338 of implant 14. In this regard, implant 14 can include an increasing outer diameter with each segmented section 340A-340D, as discussed above, where the first segment 340A includes an outer diameter less than an inner diameter of wall 604 of tibial bone tunnel 450, and the last segmented section 340D can include a diameter greater than the inner diameter of wall 604.

In one exemplary configuration and with reference back to FIGS. 12 and 13, each segment can include an inner diameter increasing by approximately 0.5 mm. In this regard, the first segment can include an outer diameter 0.5 mm less than the inner diameter of wall 604, and the last segment has an outer diameter 1.0 mm greater than the inner diameter of wall 604.

This configuration can provide an interference fit with the cancellous bone of the tibia 454 where the cancellous bone is compressed outward by the implant 14 to provide tibial fixation of graft strands 470, as discussed above.

Upon driving implant 14 into tibial tunnel 450 to provide the tibial fixation of graft strands 470, any graft strands extending out from the tibial tunnel 450 and implant 14 can be trimmed and removed. The optional guidewire 388, if used, is also removed. Tensioner 10 will then no longer be coupled to the tibia 454 and can be subsequently removed. In one exemplary configuration, the loops of construct 472 can be tensioned to draw graft 464 into the femoral tunnel and proximate passage portion 494, while stopping short of fully tensioning the loops to thereby provide for further tensioning of the loops after tibial fixation of the graft has occurred, as discussed above. In this configuration, the graft 464 can be tensioned a third time, if desired, after removal of tensioner 10 by further tensioning the first and second ends 482, 486 extending from the joint space (FIG. 21). Tensioning the ends 482, 486 further reduces the size of the loops and thus applies additional tension to the graft strands 470 that are now fixed to tibia 454 after the first and second tensions. After tensioning is completed, excess ends 482, 486 extending from tibial tunnel 450 can be removed.

Figure 15:
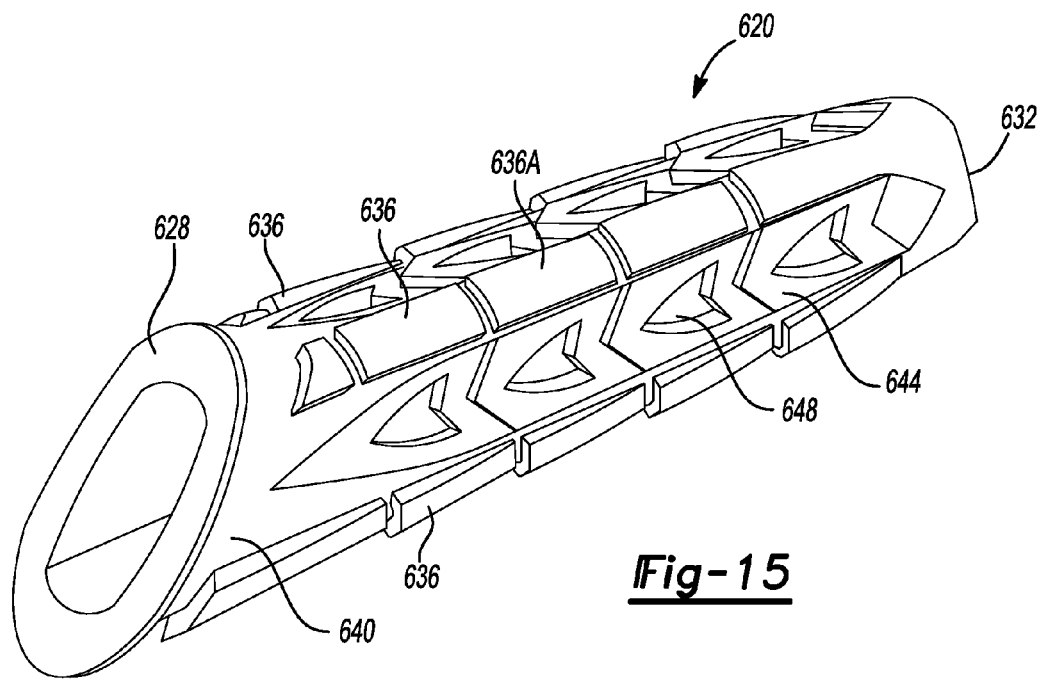
Figure 16:
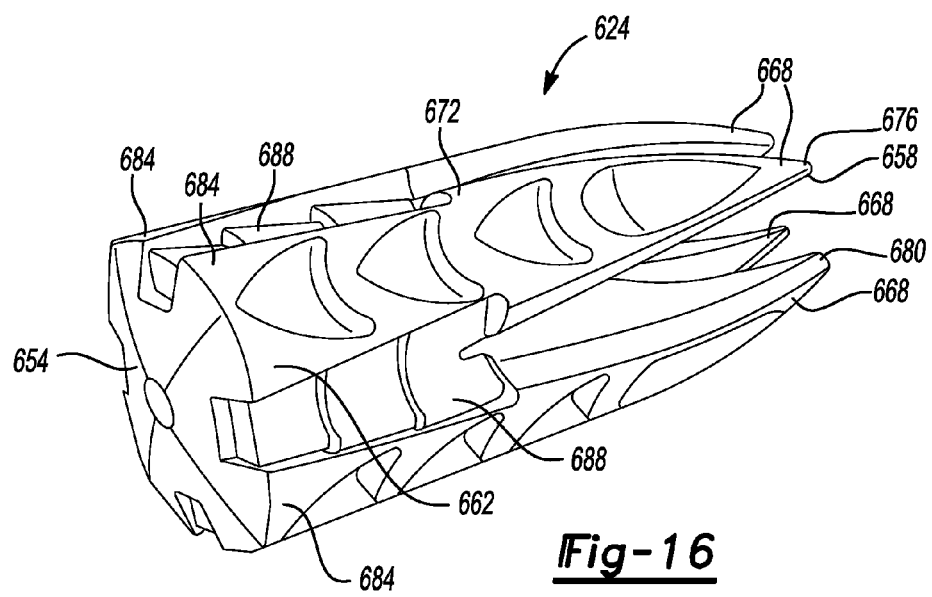

Turning now to FIGS. 15-16, alternative implants 620 and 624 will now be discussed according to various aspects of the present teachings. With particular reference to FIG. 15, implant 620 can include an open proximal end 628 and a closed or substantially closed distal end 632 similar to implant 14. Implant 620 can also be configured for use with tensioner 10 in a similar manner as implant 14. As can be seen in FIG. 15, proximal end 628 can be angled at 45 degrees relative to a longitudinal axis of implant 620 so as to be substantially parallel or parallel to the tibia 454 upon implantation. Implant 620 can include four longitudinal extending rib configurations 636 to separate an outer surface 640 into four circumferential quadrants, similar to implant 14 discussed above. In the exemplary configuration illustrated, each rib configuration 636 can include a plurality of segments 636A.

The outer surface 640 between adjacent rib configurations 636 can include a concave shape 644 in cross section and can include a plurality of graft engaging features 648. In the exemplary configuration illustrated, the graft engaging features 648 can include various depressions and/or projections configured to engage the graft strands 470. Implant 620 can also include an increasing outer diameter or dimension from the distal end 632 toward the proximal end 628. In one exemplary configuration, the distal end 632 can include an outer diameter less than the inner diameter of wall 604 of the tibial tunnel 450 and the proximal end 628 can include an outer diameter greater than the inner diameter of wall 604.

With particular reference to FIG. 16, implant 624 can include a proximal end 654 and a distal end 658, and can also be configured for use with tensioner 10 in a manner similar to implant 14. Implant 624 can include a body 662 extending from the proximal end 654 toward the distal end 658 that transitions into four axially extending and circumferentially spaced apart leg members 668. Each leg member 668 can include a proximal end 672 having a width greater than a distal end 676, as shown in FIG. 16. In the exemplary configuration illustrated, the distal ends 676 of each leg member can terminate in a distal tip or point 680. The body 662 can include four longitudinally extending protrusions 684 each axially aligned with a respective leg member 668, as shown in FIG. 16. In this regard, each graft strand 470 can be positioned in the space between each leg member 668 and the corresponding recessed area 688 between each protrusion 684.

Turning now to FIG. 17, another alternative implant 700 is illustrated for use in tibial fixation of graft strands 470 in accordance with an aspect of the present teachings. In one exemplary configuration, implant 700 can be used in conjunction with tensioner 10, where tensioner 10 is used to tension graft strands 470 in the manner discussed above. Implant 700 can be used to compress the graft strands 470 between the implant 700 and the inner diameter of wall 604 of tibial tunnel 450. Implant 700 can include a proximal end 704 and a distal end 708 terminating in a distal tip 712. Proximal end 704 can include a head member 716 configured to receive an impact or driving force to drive implant 700 into tibial tunnel 450 about graft strands 470, as shown for example in FIG. 17. A graft engaging member 720 can be positioned adjacent head member 716 about a body 724 of implant 700 and can include a graft engaging surface 728. Graft engaging surface 728 can include a plurality of teeth or projections 732 configured to engage graft strands 470 and aid in fixing strands 470 to tibia 454.

Implant 700 can also include an aperture 736 extending through the implant proximate the head member 716 and transverse to a longitudinal axis of implant 700. In the exemplary configuration illustrated in FIG. 17, aperture 736 can be positioned between or substantially between head member 716 and graft engaging member 720, and can receive a fastener 740 in securing implant 700 to the tibia 454. A counterbore or countersink 744 can be formed in the tibia 454 at the entrance of tibial tunnel 450 to receive the graft engaging member 720, as also shown in FIG. 17. In one exemplary configuration, the body 724 of implant 700 can include a diameter or width that forms an interference fit relative to the inner wall of the tibial tunnel 450.

Figure 29:
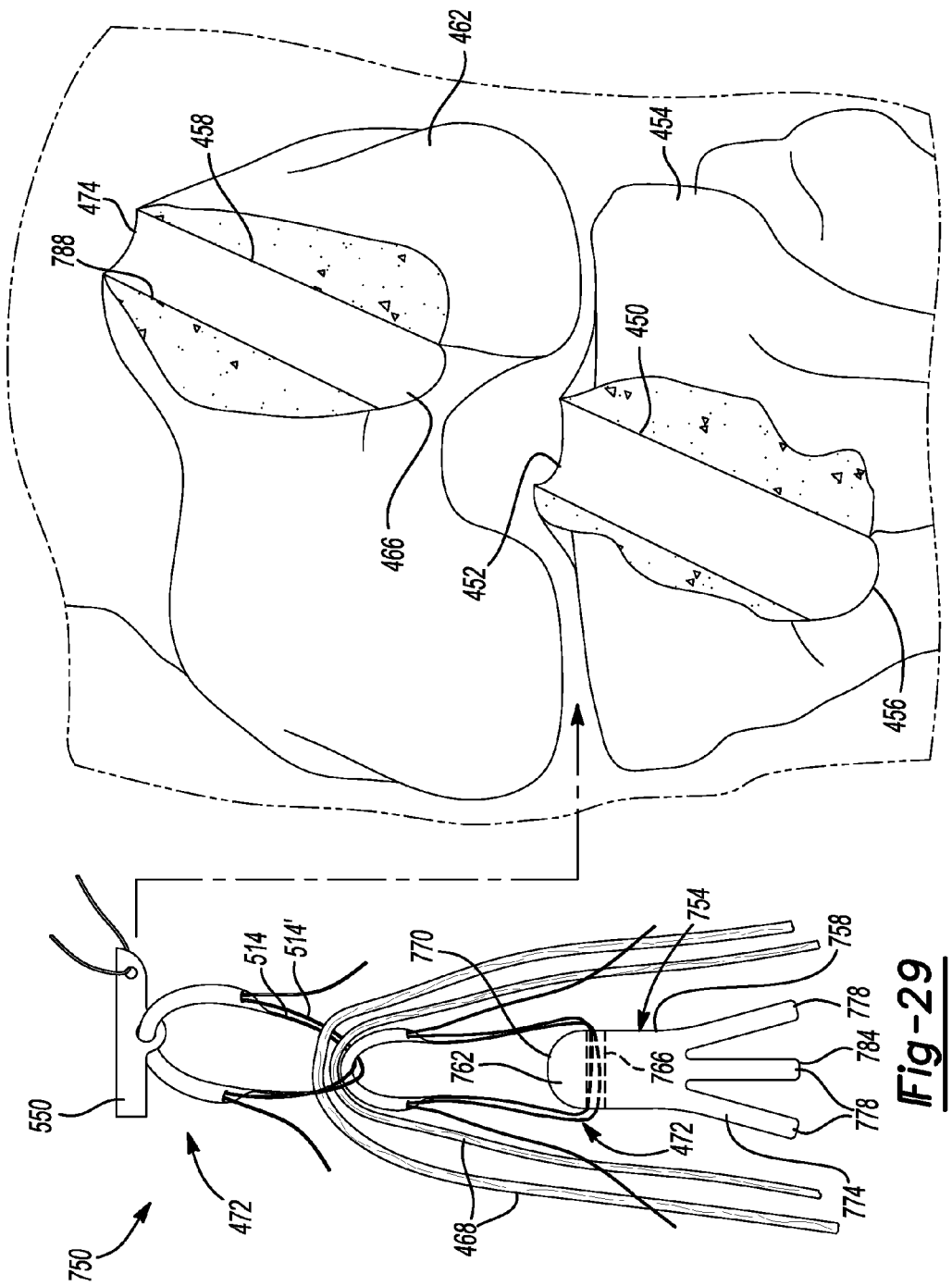
FIGS. 29-30 are views depicting another exemplary ACL reconstruction procedure in accordance with the teachings of the present disclosure.
Figure 30:
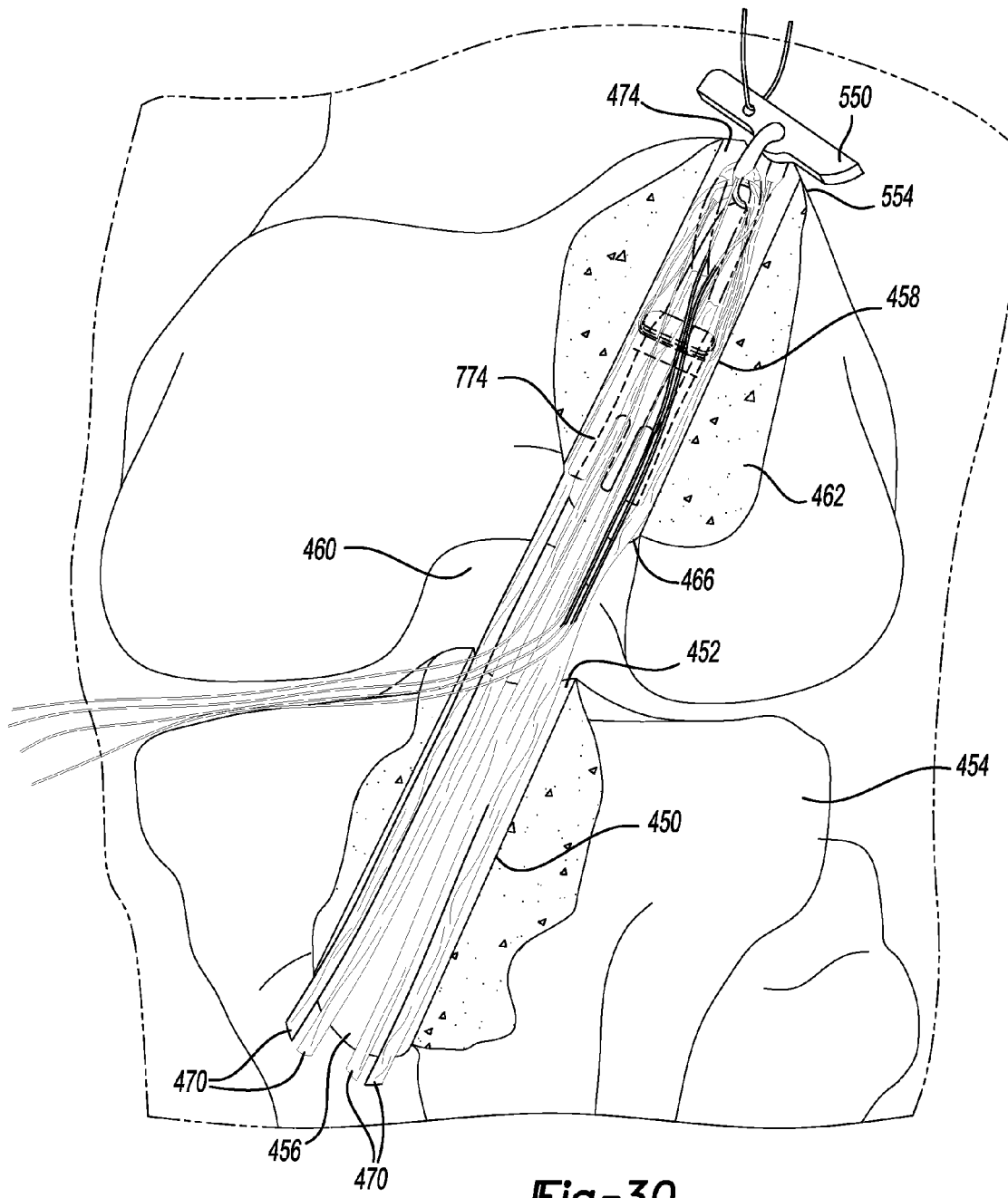

Turning now to FIGS. 29-30, a femoral fixation arrangement and associated technique will now be described in accordance with an aspect of the present teachings. With particular reference to FIG. 29, a flexible member construct assembly 750 is shown and can include a first flexible member construct 472 coupled to fixation member 550 in the manner discussed above. A pair of graft bundles 468 can also be looped over construct 472 in the manner discussed above. In addition, a second flexible member construct 472 can be coupled to the loops 514, 514' and to a graft fixation member 754, as shown in FIG. 29.

Graft fixation member 754 can include a body 758 having a first portion 762 defining an aperture 766 adjacent a proximal end 770 thereof, and a second portion 774 having a plurality of leg members, such as four leg members 778, extending to and defining a distal end 784 of fixation member 754. Aperture 766 can receive a portion of the second flexible member construct 472 to couple fixation member 754 to the first flexible member construct 472, as discussed above and shown in FIG. 29. The first portion 762 of body 758 can include a diameter or width substantially equal to or greater than an inner wall 788 of femoral tunnel 458 so as to be received in femoral tunnel 458 about graft strands 470 in an interference fit relationship. Alternatively, first portion 762 can include a diameter less than inner wall 788 so as to be received about graft strands 470 in a non-interference fit manner relying on leg members 778 for the femoral fixation, as will be discussed below. The leg members 778 can be biased radially outward from first portion 762 so as to have an increasing diameter or width in a direction toward distal end 784, as shown in FIG. 29. Graft fixation member 754 can include any number of legs 778, such as three or four legs to secure and separate the four grafts strands 470.

In use, and with reference to FIG. 30, the fixation member 550 can be drawn through the joint space 460 and up through the femoral tunnel 458 such that the fixation member 550 engages the outer surface 554 of the femur 462 at exit 474 in the manner discussed above. The free ends of the first flexible construct 472 can be tensioned to draw the graft into the femoral tunnel 458 relative to fixation member 550, as shown in FIG. 30 and discussed above with reference to FIG. 21. At this point, the graft fixation member 754 can remain outside of the femoral tunnel adjacent the joint space 460 and near the opening 466. The free ends 482, 486 of the first and second flexible member constructs 472 can extend from the femoral tunnel out through the joint space 460 and/or can extend through the femoral and tibial tunnels 458, 450. In one exemplary configuration, the free ends of the first and second flexible member constructs can both extend out of the joint space 460 to provide for tensioning/drawing the graft strands 470 and/or the graft fixation member 754 after implant 14 or another tibial fixation member is implanted into tibial tunnel 450. The graft strands 470 can then be fed into and through the tibial tunnel 450 starting from the joint space side. Once the graft strands 470 are fed though the tibial tunnel 450, the grafts strands 470 can be tensioned using tensioner 10 in the manner discussed above or another appropriate tensioning arrangement.

Having tensioned graft strands 470, the free ends of the second flexible construct 472 can be tensioned to draw the graft fixation member 754 into the femoral tunnel 458 via the joint space 460. As the graft fixation member 754 is drawn into the femoral tunnel 458, the leg members 778 can be compressed against their biased outward position thereby exerting a force on the inner wall 788 of femoral tunnel 458 to provide femoral fixation and separation of the graft strands 470. In one exemplary configuration, the graft fixation member 754 can be drawn into the femoral tunnel 458 such that the distal end 784 of the graft fixation member 754 is positioned at the entrance 466 of the femoral tunnel 458 to provide the femoral fixation of graft strands 470 at the location where the graft extends from the femoral tunnel 458 into the joint space 460. This configuration can prevent movement of the graft strands 470 at the entrance 466 between flexion and extension and thereby increase wear resistance and stability of the graft 464.

The graft strands 470 can then be fixed to the tibia 454 using the aperture fixation technique discussed above in connection with tensioner 10 or another tibial tensioning and fixation technique. Once the graft strands 470 are fixed to the tibia 454, the free ends of the first flexible member construct 472 can optionally be tensioned to reduce the size of loops 514, 514' and thereby add additional tension to the graft strands 470 after tibial fixation. By having the free ends 482, 486 of the first and second flexible member constructs 472 extend from the femoral tunnel 458 out through the joint space 460, tensioning of the first and/or second flexible member constructs 472 can be accomplished after tibial fixation of the graft strands 470, which can obstruct the tibial tunnel 450.

Figure 31A:
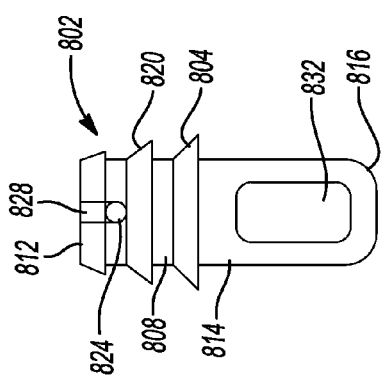
FIGS. 31A-32 are views depicting another exemplary ACL reconstruction procedure in accordance with the teachings of the present disclosure.
Figure 31B:
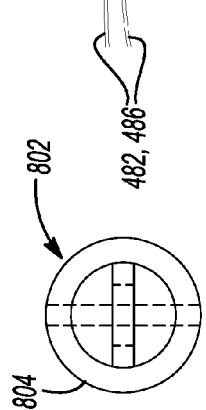

With additional reference to FIGS. 31A-32, another femoral fixation member and associated technique will now be discussed in accordance with an aspect of the present teachings. A flexible member construct assembly 800 is shown and can include a first flexible member construct 472, fixation member 550, and a fixation member 802. Fixation member 802 can include a body 804 having a first portion 808 defining a proximal end 812 and a second portion 814 extending therefrom and defining a distal end 816. The first portion 808 can include annular ribs or barbs 820 sized and shaped to provide for movement in one axial direction, such as into the femoral tunnel 458, and to resist movement in an opposite direction as shown in FIG. 31A. The first portion 808 can include a transverse aperture 824 adjacent the proximal end 812 that is configured to receive the loops 514, 514' of flexible member construct 472 to couple fixation member 802 thereto. A pair of notches 828 can be provided on opposite lateral sides of the first portion 808 in alignment with the aperture 824 for receiving a portion of the flexible member construct 472 therein.

Figure 32:
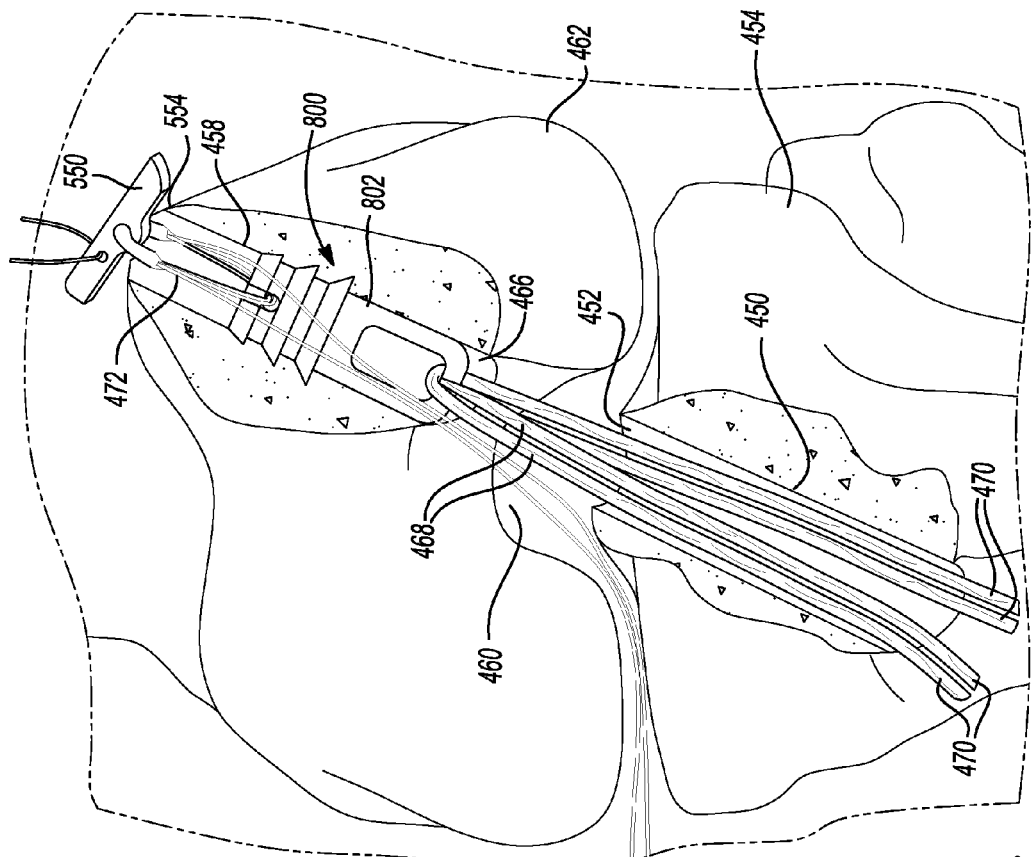

The second portion 814 can define an opening 832 configured to receive graft bundles 468, as shown in FIG. 32. Fixation member 550 of flexible member construct assembly 800 can be drawn into the femoral tunnel 458 from the joint space 460 or up through the tibial tunnel 450 and can be fixed to the outer surface 554 of the femur 462 in the manner discussed above. The free ends 482, 486 of the flexible member construct 472 can then be tensioned to draw the fixation member 802 into the femoral tunnel 458 such that the distal end 816 of fixation member 802 is at the entrance 466 adjacent the joint space 460. This configuration can thus also provide femoral fixation of the graft strands 470 at the entrance 466 and exit 474 of the femoral tunnel 458. The graft strands 470 can be tensioned using tensioner 10 or another suitable tensioning technique and can be fixed to the tibia using implant 14 or another suitable implant, such as those discussed herein.

With additional reference to FIGS. 33A-34, another flexible member construct assembly 850 is shown in accordance with an aspect of the present teachings. Flexible member construct assembly 850 can also include the first flexible member construct 472, fixation member 550 and fixation member 802 of assembly 800 discussed above. A second flexible member construct 472 can be coupled to opening 832 along with graft bundles 468, as shown for example in FIG. 34. A tibial fixation member 854 can be used with assembly 850 in place of implant 14. As will be discussed below, fixation member 854 can be separate from flexible construct 472 such that it can be placed inside loops 514, 514' at an appropriate time during the procedure.

Fixation member 854 can include a body 858 having a first portion 862 defining a proximal end 866 and a second portion 870 extending therefrom and defining a distal end 874. First portion 862 can include an outer diameter or width sized to provide an interference fit with tibial tunnel 450 so as to provide aperture fixation of graft strands 470 when implanted in tibial tunnel 450 about graft strands 470. First portion 862 can include four axially extending concave portions 878 to receive graft strands 470 similar to the quadrants 356. The second portion 870 can include a plurality of radially outwardly extending tabs or projections 882 at the distal end 874 to provide a positive stop for fixation member 854 relative to tibial tunnel 450. In this regard, projections 882 can include an outer diameter or dimension greater than the inner diameter of tibial tunnel 450.

In use, fixation member 854 of assembly 850 can be drawn into the femoral tunnel 458 and positioned on the outer surface of the femur 462 in a manner similar to that discussed above in connection with assembly 800. If fixation member 802 is fed though joint space 460, then graft strands 470 and the loops and free ends of the second flexible construct 472 can be fed into and through the tibial tunnel 450. The free ends of the first flexible construct 472 can be tensioned to draw the fixation member 802 and graft strands 470 into the femoral tunnel 458. As discussed above, the free ends can be tensioned so as to position the distal end of fixation member 802 adjacent the exit 466 of femoral tunnel 458, as shown in FIG. 34. The grafts strands 470 extending through the tibial tunnel can then be tensioned using tensioner 10 or with another technique, and the fixation member 854 can then be implanted into tibial tunnel 450 about graft strands 470 to provide tibial fixation of strands 470. To implant fixation member 854 into tibial tunnel 450, the loops 514, 514' extending from tibial tunnel 450 can be looped around fixation member 854 and then tensioned to draw fixation member into tibial tunnel 450 about graft strands 470 to fix strands 470 to the tibia 454. Fixation member 854 can be drawn into tibial tunnel 450 until projections 882 engage an outer surface of the tibia adjacent tunnel 450, as shown in FIG. 34.

In an exemplary alternative configuration, the first flexible construct 472 can be tensioned to draw fixation member 802 partially into the femoral tunnel 458, but short of the desired position so as to provide an ability to further draw fixation member into the femoral tunnel 458 after tibial fixation of strands 470, as will be discussed below. The fixation member 854 can then be positioned in loops 514, 514' and pulled into the tibial tunnel to fix graft strands 470 to the tibia in the manner discussed immediately above. After tibial fixation of strands 470, the first flexible construct 472 can be further tensioned to further draw fixation member 802 into the desired position in the femoral tunnel 458 and at the same time tension graft strands 470 to the desired tension.

Turning now to FIGS. 35A-36, another tibial fixation member 900 is shown in accordance with an aspect of the present teachings. Tibial fixation member 900 can include a proximal end 904, a distal end 908 and a body 912 extending therebetween. Body 912 can include a stepped configuration 916 having four radially outward extending members 920 forming four quadrants for graft strands 470. A notch 924 can extend along opposite lateral side of the fixation member 900 for receipt of a portion of flexible member construct 472, as will be discussed below in greater detail. Distal end 908 can include a projection 928 having a notch 932 formed therein and configured to receive suture loops 514, 514'.

In use, fixation member 900 can be placed in loops 514, 514' extending from tibial tunnel 450 and drawn into a counterbore 936 formed in the tibia 454 to fix graft strands 470 to tibia 454, as shown for example in FIG. 34. In this regard, fixation member 900 can be used as an alternative to fixation member 802 with assembly 800 to effect tibial fixation of graft strands 470. Fixation member 900 can also be used as an alternative to fixation member 700 discussed above in connection with FIG. 17. It should be appreciated that fixation members 854 and 900 can also be used as an alternative to fixation member 754 discussed above in connection with FIGS. 29 and 30. In this regard, second flexible member construct 472 of construct assembly 750 can be looped over one of fixation members 854 or 900 in place of being coupled to fixation member 754.

Turning now to FIGS. 37A-40, a pair of alternative graft fixation members will now be discussed in accordance with various aspects of the present teachings. With particular reference to FIGS. 37A-38, a graft fixation assembly 950 is shown and can include an outer sheath member 954 and an inner or plug member 958. Fixation assembly 950 can be used for either femoral or tibial fixation of graft strands 470, as will be discussed below. Sheath member 954 can include four legs 962 extending from a common tip 966. Each leg member can increasingly extend radially outward from a proximal end 970 to a distal end 974. The legs 962 can include an outer diameter or dimension greater than a corresponding inner diameter of the tibial or femoral tunnels. Each leg 962 can include a projection 978 extending radially outward therefrom and configured to act as a positive stop when the sheath 954 is positioned in the femoral or tibial tunnels.

Plug member 958 can include a body 984 having a proximal end 988 and a distal end 992. Body 984 can include a stepped configuration 996 defining a plurality of segments 1002 having an increasing diameter from the proximal end 988 to the distal end 992, as shown in FIG. 38. Plug member 958 can be received in the sheath member 954 inside of legs 962 so as to expend legs 962 outward between the four graft strands 470 and against a wall of the femoral or tibial tunnels. In this regard, the diameter of the distal end of plug member 958 can be sized to create an interference fit with the femoral or tibial tunnels when received in the sheath member 954 that is positioned in one of the femoral or tibial tunnels. The proximal end 988 of plug member 958 can include an aperture 1006 formed therein and configured to receive loops of flexible member construct 472, as will be discussed below.

In use, the loops of the first or second flexible member construct 472 (depending on whether the fixation assembly 950 will be used for femoral or tibial fixation) can be passed through an aperture 982 in the sheath member 954 and coupled to plug member 958 via aperture 1006. For example, and with reference back to FIG. 29, fixation assembly 950 can be used in place of fixation member 754 where sheath member 954 and plug member 958 are coupled to the first flexible member construct 472. Alternatively, in another exemplary configuration and with reference back to FIG. 34, fixation assembly 950 can be used for tibial fixation where sheath member 954 and plug member 958 are coupled to the second flexible member construct 472 of assembly 850 in place of fixation member 854.

In either femoral or tibial fixation, the sheath member 954 can be positioned in the respective bone tunnel between graft strands 470 by sliding the sheath member 954 about the loops 514, 514' until the projections 978 abut an outer surface of the respective tunnel similar to fixation member 854 shown in FIG. 34. The corresponding flexible member construct 472 can then be tensioned to draw plug member 958 into sheath member 954 thereby expanding legs 962 into compressed engagement with surrounding bone of the bone tunnel to separate and fix graft strands 470 to the respective femur or tibia.

With additional reference to FIGS. 39A-40, graft fixation assembly 1012 will now be discussed. Graft fixation assembly 1012 is similar to graft fixation assembly 950 and can also be used for either femoral or tibial graft fixation in a similar manner as assembly 950. Graft fixation assembly 1012 can include an outer sheath member 1016 and a plug member 1020 configured to be received in the sheath member 1016, as will be discussed below. Sheath member 1016 can include four leg members 1024 extending from an open proximal end 1028 to an open distal end 1032, as shown in FIGS. 39A and 39B. Each leg member 1024 can extend radially outward as it extends from the proximal end 1028 to the distal end 1032 such that sheath member 1016 includes an increasing diameter or width from the proximal end 1028 to the distal end 1032, as shown in FIG. 39A. In one exemplary configuration, the diameter at the distal end can be larger than an inner diameter of the femoral or tibial tunnel so as to create an interference fit when the sheath member is positioned therein. Each leg member 1024 can include a radially outward projection 1036 configured to serve as a positive stop in a similar manner as projections 978 of fixation assembly 950.

Plug member 1020 can also be similar to plug member 958 and can include a body 1044 having a proximal end 1048 and a distal end 1052. Proximal end 1048 can define an aperture 1056 for receiving flexible member construct 472 and the body can include an increasing diameter from the proximal end 1048 to the distal end 1052. Similar to plug member 958, a diameter of the distal end 1052 of plug member can be greater than a diameter of the proximal end 1028 of legs 1024 so as to expand the legs into compressive engagement with graft strands 470 and surrounding bone of the femur or tibia. Plug member 1020 can also include notches or depressions 1058 configured to engage the leg members 1024 and prevent rotation of plug member 1020 relative to sheath member 1016.

Figure 41:
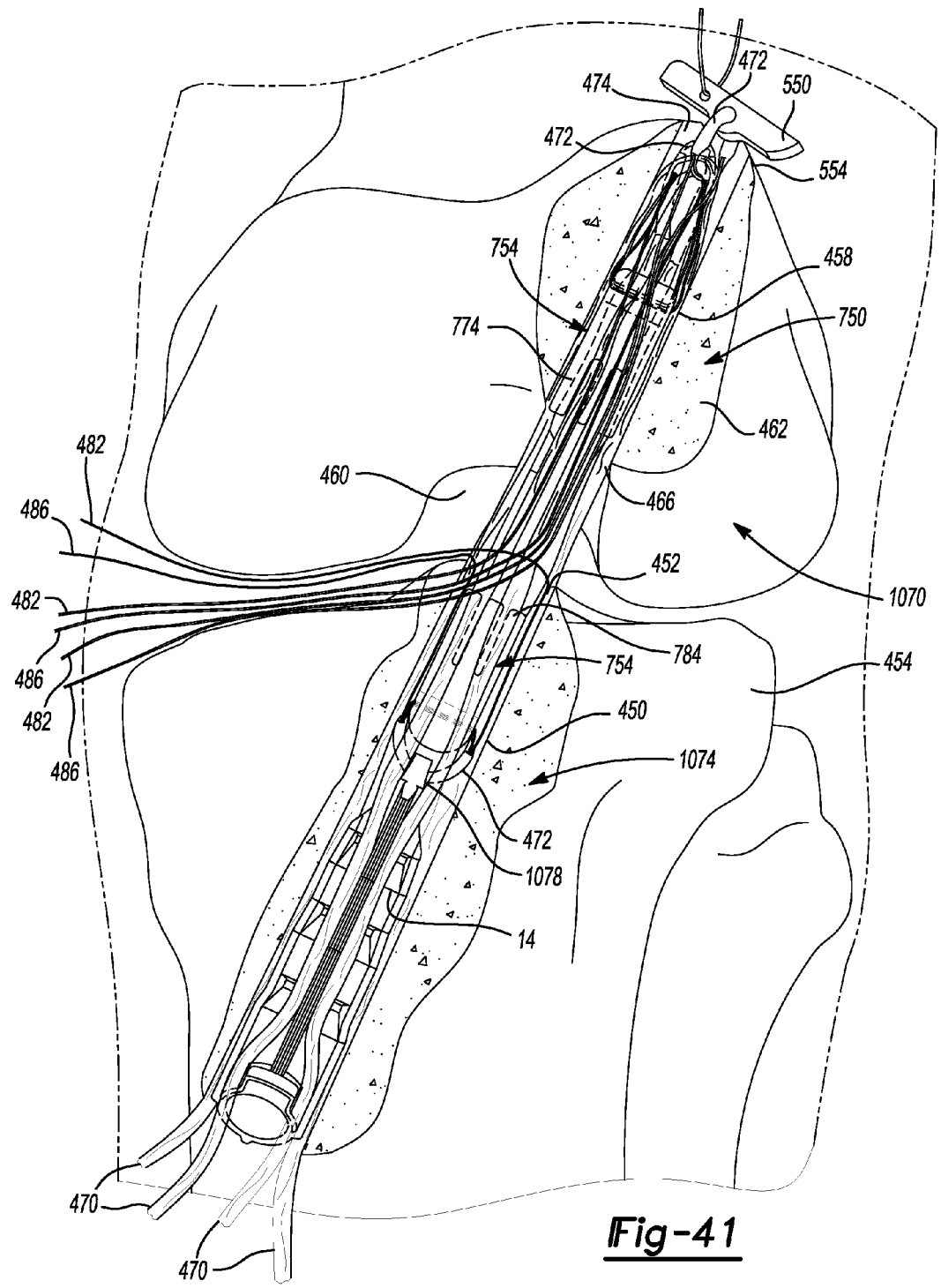
FIG. 41 depicts another exemplary ACL reconstruction procedure in accordance with the teachings of the present disclosure.

With additional reference to FIG. 41, another flexible member construct assembly 1070 is shown in accordance with an aspect of the present teachings. As will be discussed in greater detail below, construct assembly 1070 can be used to provide femoral and tibial fixation at the entrance and exit of the tibial tunnel 450 and the femoral tunnel 458. Construct assembly 1070 can include flexible member construct assembly 750 for use in femoral fixation in the manner discussed above and as shown in FIG. 41 with reference to FIGS. 29-30. Alternatively, construct assembly 1070 can use construct assembly 800 in the manner discussed above for use in femoral fixation at the entrance 466 and exit 474 of femoral tunnel 458, as shown in FIGS. 31A-32.

Construct assembly 1070 can also include a tibial fixation assembly 1074 for use in fixing the tensioned graft strands 470 relative to the entrance 452 and exit 456 of tibial tunnel 450, as shown in FIG. 41. In one exemplary configuration, tibial fixation assembly 1074 can include implant 14 having a transverse bore 1078 adjacent the distal end 334 with a third flexible member construct 472 coupled thereto. In the exemplary configuration illustrated, fixation member 754 can be coupled to implant 14 via transverse bore 1078 and third flexible member construct 472, as shown in FIG. 41. It should be appreciated that a notch or projection could alternatively be used on implant 14 in place of bore 1078 to provide for coupling third flexible member construct 472 and associated fixation member 754 to implant 14 during the procedure. It should also be appreciated that other tibial fixation members discussed herein can be alternatively used with tibial fixation assembly 1074 in place of implant 14.

In operation, construct assembly 1070 can be used to provide femoral and tibial fixation of graft strands 470. In the exemplary configuration illustrated, construct assembly 750 can be used to draw graft strands 470 into femoral tunnel 458 and fix graft strands 470 relative to outer surface 554 and entrance 466, as shown in FIG. 41 and discussed above. The tibial fixation assembly 1074 can then be used to provide tibial fixation of the tensioned graft strands 470 relative to the entrance 452 and exit 456 of tibial tunnel 450.

In this regard, fixation member 754 can be positioned relative to the joint space 460 such that third flexible member construct assembly 472 extends into joint space 460 and down through tibial tunnel 450 to implant 14 adjacent exit 456. Once implant 14 is implanted into tibial tunnel 450 to fix the tensioned graft strands 470 relative thereto, free ends 482, 486 of third construct 472 can be tensioned to draw fixation member 754 into tibial tunnel 450 via joint space 460 and fix the tensioned graft strands 470 relative to entrance 452 of tibial tunnel 450. In the exemplary configuration illustrated, fixation member 754 can be drawn into tibial tunnel 450 such that distal end 784 is adjacent entrance 452.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A tensioner system for use in graft strand tensioning and fixation in a knee reconstruction procedure, comprising:
a handle assembly, the handle assembly includes a hollow outer handle body and an inner handle body slidably received within the outer handle body;
a tensioner assembly coupled relative to the handle assembly, the tensioner assembly including:
an arm support member rotatably coupled to a distal end of the inner handle body; and
first and second arm members each rotatably coupled to lateral sides of the arm support member, each arm member including at least one graft attachment area adapted to be coupled to a graft strand, the arm support member configured to rotate about an axis perpendicular to a longitudinal axis of the tensioner system and perpendicular to an axis of rotation of each of the first and second arm members;
a drive shaft slidably received through and supported by the handle assembly such that proximal and distal ends of the drive shaft extend beyond respective proximal and distal ends of the handle assembly; and
a ratcheting member slidably received in the outer handle body and including a plurality of ratchet teeth in selective engagement with a pawl carried by the outer handle body, the ratchet teeth configured to maintain a position of the outer handle body relative to the ratcheting member upon movement of the outer handle body relative to the ratcheting member.

2. The tensioner system of claim 1, further comprising an implant coupled to the distal end of the drive shaft.

3. The tensioner system of claim 2, wherein the implant includes a body having a proximal end, a distal end and an inner bore extending from the proximal end partially toward the distal end, and wherein the distal end of the drive shaft is received in the bore of the implant and the proximal end of the drive shaft includes an impact plate.

4. The tensioner system of claim 3, wherein the implant includes a plurality of segmented portions having an increasing diameter from the distal end to the proximal end.

5. The tensioner system of claim 3, wherein the implant further comprises four longitudinally extending ribs each equally circumferentially spaced apart from each other around an outer surface of the implant.

6. The tensioner system of claim 3, wherein the implant includes an angled surface at the proximal end adapted to correspond to an angle of a tibial bone tunnel relative to a longitudinal axis of the tibia such that a length of the implant along a superior surface is less than a length of the implant along an opposite inferior surface.

7. The tensioner system of claim 6, further comprising a projection extending radially outward from the proximal end at the superior surface of the implant.

8. The tensioner system of claim 2, wherein the handle assembly, arm support member, drive shaft and implant are cannulated.

9. The tensioner system of claim 2, further comprising:
a self-locking adjustable flexible member construct having a pair of adjustable loops adapted to be coupled to graft strands; and
a fixation member coupled to the adjustable flexible member construct;
wherein the fixation member is adapted to fix the adjustable flexible member construct relative to a bone tunnel.

10. The tensioner system of claim 1, further comprising a spring positioned within the outer handle body about the inner handle body and biasing the arm support member and arms in a direction toward and against the outer handle body, wherein movement of the outer handle body relative to the inner handle body increases a longitudinal length of the tensioner system.

11. The tensioner system of claim 1, wherein when the arm support member and arms are biased against the outer handle body, the arm support member and arms are locked in a non-deployed or deployed position; and
wherein when tension is applied to the tensioner assembly such that the outer handle body moves apart from the arms and arm support member, the arms and arm support member are free to independently rotate about each of their respective axes.

12. The tensioner system of claim 1, further comprising a tension release member coupled to the outer handle body and in engagement with the pawl, the tension release member configured to allow engagement of the pawl with the ratchet teeth in a first position and to disengage the pawl from the ratchet teeth upon movement of the tension release member from the first position to a second position.

13. The tensioner system of claim 1, wherein the arm support member is rotatably coupled to the inner handle body at a longitudinally central portion of the arm support member such that each arm is positioned on an opposite side of and laterally spaced apart from the inner handle body and the ratcheting member.

14. The tensioner system of claim 1, wherein the ratcheting member includes a throughbore slidably receiving a portion of the drive shaft and a C-shaped distal end adapted to be aligned with a tibial bone tunnel and receive the drive shaft therethrough.

15. The tensioner system of claim 14, wherein the ratcheting member further comprises a bone engaging member protruding from the distal end thereof beyond a bone engaging surface of the C-shaped distal end.

16. The tensioner system of claim 1, wherein the inner handle body includes a U-shaped channel having an open end, and wherein the ratcheting member includes a second side opposite a first side having the ratchet teeth, the second side slidably abutting the open end of the U-shaped channel of the inner handle body.

17. The tensioner system of claim 16, wherein the drive shaft is received within the U-shaped channel of the inner handle body so as to have at least a portion surrounded by the inner handle body and the ratcheting member.

18. The tensioner system of claim 1, wherein each arm member includes a pair of graft strand attachment portions at opposed ends thereof such that the tensioner assembly is adapted to be coupled to four graft strands with each arm adapted to be coupled to a pair of the four graft strands.

19. The tensioner system of claim 18, wherein the attachment portions include slots adapted to receive a respective suture coupled to each graft strand.

20. The tensioner system of claim 1, wherein the inner handle body includes a scale positioned about a proximal end thereof having indicia indicative of an amount of tension being applied by the tensioner system.

21. A tensioner system for use in graft strand tensioning and fixation in a knee reconstruction procedure, comprising:

a handle assembly including a hollow outer handle body and an inner handle body slidably received within the outer handle body, an arm support member rotatably coupled to a distal end of the inner handle body;

a tensioner assembly coupled relative to the handle assembly;

a ratcheting member slidably received in the outer handle body and including a plurality of ratchet teeth in selective engagement with a pawl carried by the outer handle body, the ratchet teeth configured to maintain a position of the outer handle body relative to the ratcheting member upon movement of the outer handle body relative to the ratcheting member; and a drive shaft slidably received through and supported by the handle assembly such that proximal and distal ends of the drive shaft extend beyond respective proximal and distal ends of the handle assembly;

wherein the ratcheting member includes a throughbore slidably receiving a portion of the drive shaft and a C-shaped distal end adapted to be aligned with a tibial bone tunnel and receive the drive shaft therethrough.

22. The tensioner system of claim 21, wherein the tensioner assembly includes:

first and second arm members each rotatably coupled to lateral sides of the arm support member, each arm member including at least one graft attachment area adapted to be coupled to a graft strand, the arm support member configured to rotate about an axis perpendicular to a longitudinal axis of the tensioner system and perpendicular to an axis of rotation of each of the first and second arm members.

23. The tensioner system of claim 22, further comprising a spring positioned within the outer handle body about the inner handle body and biasing the arm support member and arms in a direction toward and against the outer handle body, wherein movement of the outer handle body relative to the inner handle body increases a longitudinal length of the tensioner system.

24. The tensioner system of claim 22, wherein when the arm support member and arms are biased against the outer handle body, the arm support member and arms are locked in a non-deployed or deployed position; and wherein when tension is applied to the tensioner assembly such that the outer handle body moves apart from the arms and arm support member, the arms and arm support member are free to independently rotate about each of their respective axes.

25. The tensioner system of claim 22, wherein the arm support member is rotatably coupled to the inner handle body at a longitudinally central portion of the arm support member such that each arm is positioned on an opposite side of and laterally spaced apart from the inner handle body and the ratcheting member.

26. The tensioner system of claim 21, further comprising an implant coupled to the distal end of the drive shaft.

27. The tensioner system of claim 21, further comprising a tension release member coupled to the outer handle body and in engagement with the pawl, the tension release member configured to allow engagement of the pawl with the ratchet teeth in a first position and to disengage the pawl from the ratchet teeth upon movement of the tension release member from the first position to a second position.

28. The tensioner system of claim 21, wherein the ratcheting member further comprises a bone engaging member protruding from the distal end thereof beyond a bone engaging surface of the C-shaped distal end.

29. The tensioner system of claim 21, wherein the inner handle body includes a U-shaped channel having an open end, and wherein the ratcheting member includes a second side opposite a first side having the ratchet teeth, the second side slidably abutting the open end of the U-shaped channel of the inner handle body.

30. A tensioner system for use in graft strand tensioning and fixation in a knee reconstruction procedure, comprising:

a handle assembly including a hollow outer handle body and an inner handle body slidably received within the outer handle body, an arm support member rotatably coupled to a distal end of the inner handle body;

a tensioner assembly coupled relative to the handle assembly, the tensioner assembly including first and second arm members each rotatably coupled to lateral sides of the arm support member;

a ratcheting member slidably received in the outer handle body and including a plurality of ratchet teeth in selective engagement with a pawl carried by the outer handle body, the ratchet teeth configured to maintain a position of the outer handle body relative to the ratcheting member upon movement of the outer handle body relative to the ratcheting member; and a drive shaft slidably received through and supported by the handle assembly such that proximal and distal ends of the drive shaft extend beyond respective proximal and distal ends of the handle assembly;

wherein when the arm support member and arms are biased against the outer handle body, the arm support member and arms are locked in a non-deployed or deployed position; and wherein when tension is applied to the tensioner assembly such that the outer handle body moves apart from the arms and arm support member, the arms and arm support member are free to independently rotate about each of their respective axes.

31. The tensioner system of claim 30, each arm member including at least one graft attachment area adapted to be coupled to a graft strand, the arm support member configured to rotate about an axis perpendicular to a longitudinal axis of the tensioner system and perpendicular to an axis of rotation of each of the first and second arm members.

32. The tensioner system of claim 30, further comprising an implant coupled to the distal end of the drive shaft.

33. The tensioner system of claim 30, further comprising a spring positioned within the outer handle body about the inner handle body and biasing the arm support member and arms in a direction toward and against the outer handle body, wherein movement of the outer handle body relative to the inner handle body increases a longitudinal length of the tensioner system.

34. The tensioner system of claim 30, further comprising a tension release member coupled to the outer handle body and in engagement with the pawl, the tension release member configured to allow engagement of the pawl with the ratchet teeth in a first position and to disengage the pawl from the ratchet teeth upon movement of the tension release member from the first position to a second position.

35. The tensioner system of claim 30, wherein the arm support member is rotatably coupled to the inner handle body at a longitudinally central portion of the arm support member such that each arm is positioned on an opposite side of and laterally spaced apart from the inner handle body and the ratcheting member.

36. The tensioner system of claim 30, wherein the ratcheting member includes a throughbore slidably receiving a portion of the drive shaft and a C-shaped distal end adapted to be aligned with a tibial bone tunnel and receive the drive shaft therethrough.

37. The tensioner system of claim 30, wherein the handle assembly, arm support member, drive shaft, and implant are cannulated.

38. The tensioner system of claim 30, wherein each arm member includes a pair of graft strand attachment portions at opposed ends thereof such that the tensioner assembly is adapted to be coupled to four graft strands with each arm adapted to be coupled to a pair of the four graft strands.

39. A tensioner system for use in graft strand tensioning and fixation in a knee reconstruction procedure, comprising:
    a handle assembly including a hollow outer handle body and an inner handle body slidably received within the outer handle body, an arm support member rotatably coupled to a distal end of the inner handle body;
    a tensioner assembly coupled relative to the handle assembly, the tensioner assembly including first and second arm members each rotatably coupled to lateral sides of the arm support member;
    a ratcheting member slidably received in the outer handle body and including a plurality of ratchet teeth in selective engagement with a pawl carried by the outer handle body, the ratchet teeth configured to maintain a position of the outer handle body relative to the ratcheting member upon movement of the outer handle body relative to the ratcheting member;
    a drive shaft slidably received through and supported by the handle assembly;
    a self-locking adjustable flexible member construct having a pair of adjustable loops adapted to be coupled to graft strands; and
    a fixation member coupled to the adjustable flexible member construct;
    wherein the fixation member is adapted to fix the adjustable flexible member construct relative to a bone tunnel.

* * * * *